US009694096B2

(12) United States Patent
McKay et al.

(10) Patent No.: US 9,694,096 B2
(45) Date of Patent: *Jul. 4, 2017

(54) METHODS COMPOSITIONS AND ARTICLES FOR OLFACTORY-ACTIVE SUBSTANCES

(71) Applicant: EnviroScent, Inc., Atlanta, GA (US)

(72) Inventors: Nicholas D. McKay, Atlanta, GA (US); Jeffrey S. Sherwood, Jasper, GA (US); Jeffery S. Hsieh, Marietta, GA (US); Pedro Antonio Rodriquez, Sanibel, FL (US)

(73) Assignee: ENVIROSCENT, INC., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/851,763

(22) Filed: Sep. 11, 2015

(65) Prior Publication Data

US 2015/0374869 A1    Dec. 31, 2015

Related U.S. Application Data

(63) Continuation of application No. 13/077,971, filed on Mar. 31, 2011, now Pat. No. 9,132,204.

(60) Provisional application No. 61/419,959, filed on Dec. 6, 2010, provisional application No. 61/409,627, filed on Nov. 3, 2010, provisional application No. 61/319,431, filed on Mar. 31, 2010.

(51) Int. Cl.
*A61L 9/012* (2006.01)
*A61L 9/013* (2006.01)
*A01N 25/34* (2006.01)

(52) U.S. Cl.
CPC .............. *A61L 9/012* (2013.01); *A01N 25/34* (2013.01); *A61L 9/013* (2013.01); *A61L 2209/13* (2013.01)

(58) Field of Classification Search
None
See application file for complete search history.

(56) References Cited

U.S. PATENT DOCUMENTS

| | | | |
|---|---|---|---|
| 324,853 A | 8/1885 | Laurier |
| 855,984 A | 6/1907 | Russell |
| 934,502 A | 9/1909 | Canon |
| 1,777,820 A | 10/1930 | Anenberg |
| 1,878,401 A | 9/1932 | John |
| 1,988,141 A | 1/1935 | Schaller |
| 2,120,204 A | 6/1938 | Langhorst |
| 2,303,073 A | 11/1942 | Brown |
| 2,615,754 A | 10/1952 | Lindenberg |
| 2,626,833 A | 1/1953 | Valentine |
| 2,800,457 A | 7/1957 | Green et al. |
| 3,041,288 A | 6/1962 | Anthony |
| 3,415,758 A | 12/1968 | Powell et al. |
| 3,516,941 A | 6/1970 | Matson |
| 3,575,345 A | 4/1971 | Buck, Jr. |
| 3,634,564 A | 1/1972 | Okamoto et al. |
| 3,770,856 A | 11/1973 | Ueki et al. |
| 3,870,542 A | 3/1975 | Ida et al. |
| 3,954,928 A | 5/1976 | Omori et al. |
| 4,020,156 A | 4/1977 | Murray et al. |
| 4,081,384 A | 3/1978 | Pracht |
| 4,210,487 A | 7/1980 | Driscoll |
| 4,234,627 A | 11/1980 | Schilling |
| 4,384,589 A | 5/1983 | Morris |
| 4,753,389 A | 6/1988 | Davis |
| 4,802,626 A | 2/1989 | Forbes et al. |
| 5,103,654 A | 4/1992 | Gee et al. |
| 5,112,688 A | 5/1992 | Michael |
| 5,145,842 A | 9/1992 | Driedger et al. |
| 5,372,303 A | 12/1994 | Paul |
| 5,395,047 A | 3/1995 | Pendergrass, Jr. |
| 5,437,410 A | 8/1995 | Babasade |
| 5,503,332 A | 4/1996 | Glenn |
| 5,544,812 A | 8/1996 | Torres |
| 5,578,563 A | 11/1996 | Trinh et al. |
| 5,710,406 A | 1/1998 | Garris et al. |
| 5,763,038 A | 6/1998 | Wood |
| 5,763,788 A | 6/1998 | Friedhoff et al. |
| 5,771,503 A | 6/1998 | Valimaa et al. |
| 5,940,921 A | 8/1999 | Wood et al. |
| 6,014,788 A | 1/2000 | Jaffri |
| 6,158,668 A | 12/2000 | Burgeson |

(Continued)

FOREIGN PATENT DOCUMENTS

| | | |
|---|---|---|
| CN | 102917878 | 2/2013 |
| EP | 1190725 A2 | 3/2002 |
| GB | 914421 | 1/1963 |
| GB | 1221488 | 2/1971 |
| GB | 1226448 | 3/1971 |
| GB | 1387265 | 3/1975 |
| JP | 08289925 | 11/1996 |
| JP | 2000093495 A | 4/2000 |
| JP | 2000312712 | 11/2000 |
| JP | 2006333904 | 12/2006 |

(Continued)

OTHER PUBLICATIONS

European Patent Application No. EP11763485.7, Partial Supplementary European Search Report, mailed Feb. 10, 2016, 6 pages.
U.S. Appl. No. 60/582,670, filed Jun. 24, 2004, Sherwood.
U.S. Appl. No. 61/319,431, filed Mar. 31, 2010, Sherwood.
U.S. Appl. No. 61/409,627, filed Nov. 3, 2010, Sherwood.

(Continued)

*Primary Examiner* — Melissa Fisher
(74) *Attorney, Agent, or Firm* — Kilpatrick Townsend & Stockton LLP

(57) ABSTRACT

The present invention is directed to methods, compositions and articles comprising olfactory-active compositions. An article of the present invention comprises a structural component and an olfactory-active composition. The article may control the release, release rate or absorption of the olfactory-active composition. The article may be of various shapes and sizes. A method of use of an article comprises providing fragrance to an environment.

20 Claims, 5 Drawing Sheets

(56) References Cited

U.S. PATENT DOCUMENTS

| | | |
|---|---|---|
| 6,168,088 B1 | 1/2001 | Mobley |
| 6,183,596 B1 | 2/2001 | Matsuda et al. |
| 6,194,375 B1 | 2/2001 | Ness et al. |
| 6,214,163 B1 | 4/2001 | Matsuda et al. |
| 6,248,703 B1 | 6/2001 | Finucane et al. |
| 6,261,483 B1 | 7/2001 | Frank et al. |
| 6,329,057 B1 | 12/2001 | Dungworth et al. |
| 6,575,383 B2* | 6/2003 | Dobler .................. A47K 10/38 239/52 |
| 6,688,551 B1 | 2/2004 | He et al. |
| 6,803,033 B2 | 10/2004 | McGee et al. |
| 6,921,024 B2 | 7/2005 | Donnelly et al. |
| 7,235,261 B2 | 6/2007 | Smith et al. |
| 7,741,266 B2 | 6/2010 | Bell et al. |
| 8,919,662 B2 | 12/2014 | Sherwood |
| 9,132,204 B2 | 9/2015 | McKay et al. |
| 9,149,552 B1 | 10/2015 | Do et al. |
| 9,381,266 B2 | 7/2016 | Sherwood |
| 2002/0136886 A1 | 9/2002 | He et al. |
| 2003/0024997 A1 | 2/2003 | Welch et al. |
| 2003/0211799 A1 | 11/2003 | Yao et al. |
| 2004/0001891 A1 | 1/2004 | Smith et al. |
| 2007/0187524 A1* | 8/2007 | Sherwood ........... A01M 1/2055 239/54 |
| 2007/0224232 A1 | 9/2007 | Sherwood |
| 2008/0008860 A1 | 1/2008 | Murray et al. |
| 2008/0009616 A1 | 1/2008 | Frank et al. |
| 2008/0286143 A1 | 11/2008 | Grodsky |
| 2011/0256364 A1 | 10/2011 | Boyer et al. |
| 2011/0262377 A1 | 10/2011 | McKay et al. |
| 2015/0108242 A1 | 4/2015 | Sherwood |
| 2015/0136872 A1 | 5/2015 | Sherwood |
| 2016/0089468 A1 | 3/2016 | Do et al. |
| 2016/0136317 A9 | 5/2016 | Sherwood |
| 2016/0136318 A9 | 5/2016 | Sherwood |
| 2016/0279276 A1 | 9/2016 | Sherwood |
| 2016/0279277 A1 | 9/2016 | Sherwood |

FOREIGN PATENT DOCUMENTS

| | | |
|---|---|---|
| WO | 9112029 A1 | 8/1991 |
| WO | 9807405 | 2/1998 |
| WO | 9842818 A1 | 10/1998 |
| WO | 9847477 | 10/1998 |
| WO | 9847478 | 10/1998 |
| WO | 9943667 | 9/1999 |
| WO | 02089862 A2 | 11/2002 |
| WO | 2004020566 A1 | 3/2004 |
| WO | 2006002395 | 1/2006 |
| WO | 2006002395 A2 | 1/2006 |
| WO | 2009078038 A2 | 6/2009 |
| WO | 2011123723 | 10/2011 |
| WO | 2013064501 A1 | 5/2013 |
| WO | 2016053802 A1 | 4/2016 |
| WO | 2016201089 A1 | 12/2016 |

OTHER PUBLICATIONS

U.S. Appl. No. 61/419,959, filed Dec. 6, 2010, Sherwood.
U.S. Appl. No. 62/173,264, filed Jun. 9, 2015, Mehnert et al.
U.S. Appl. No. 29/534,919, filed Jul. 31, 2015, McKay et al.
U.S. Appl. No. 14/851,763, filed Sep. 11, 2015, McKay et al.
U.S. Appl. No. 14/866,297, filed Sep. 25, 2015, Do et al.
Chinese Office Action, with English Translation, issued in Patent Application No. 2011-80026620.7, mailed Feb. 12, 2014, 12 pages.
Chinese Office Action, with English Translation, issued in Patent Application No. 2011-80026620.7, dated Nov. 14, 2014, 15 pages.
Japanese Office Action, with English translation, issued in Patent Application No. JP2013-502872, dated Oct. 28, 2014, 11 pages.
Japanese Office Action, with English translation, issued in Patent Application No. JP2013-502872, dated Jun. 30, 2015, 2 pages.
International Patent Application No. PCT/US2005/022566, International Search Report and Written Opinion, mailed Jun. 18, 2007, 6 pages.
International Patent Application No. PCT/US2005/022566, International Preliminary Report on Patentability, issued Jul. 10, 2007, 5 pages.
International Patent Application No. PCT/US2011/030842, International Search Report and Written Opinion, mailed May 23, 2011, 7 pages.
International Patent Application No. PCT/ US2011/030842, International Preliminary Report on Patentability, issued Oct. 2, 2012, 6 pages.
U.S. Appl. No. 13/077,971, Non-Final Office Action, mailed Jul. 3, 2013, 16 pages.
U.S. Appl. No. 13/077,971, Final Office Action, mailed Apr. 2, 2014, 15 pages.
U.S. Appl. No. 13/077,971, Non-Final Office Action, mailed Jul. 18, 2014, 19 pages.
U.S. Appl. No. 13/077,971, Final Office Action, mailed Jan. 2, 2015, 19 pages.
U.S. Appl. No. 13/077,971, Notice of Allowance, mailed May 8, 2015, 9 pages.
EP11763485.7, "Extended European Search Report", May 18, 2016, 11 pages.

* cited by examiner

METHODS COMPOSITIONS AND ARTICLES FOR OLFACTORY-ACTIVE SUBSTANCES

RELATED APPLICATIONS

This application is a continuation of U.S. patent application Ser. No. 13/077,971, filed Mar. 31, 2011, which claims the priority of U.S. Provisional Patent Application Serial Nos. 61/319,431, filed Mar. 31, 2010; 61/409,627, filed Nov. 3, 2010; and 61/419,959, filed Dec. 6, 2010; each of which is incorporated herein by reference in its entirety.

TECHNICAL FIELD

The various embodiments of the present invention relate generally to articles that provide olfactory-active substances, such as an article that provides odorous compounds, for example, a fragrance, and methods and compositions for making and using such articles.

BACKGROUND OF THE INVENTION

It has become a desired accessory for homes, automobiles and other spaces to provide a scented environment. Materials such as ceramics, polymers, wood and cellulose materials have been used to release a fragrance. Cotton has been used to release volatile materials, such as a fragrance, and examples are described in U.S. Pat. Nos. 2,615,754 and 5,372,303. Fabric has also been used as an absorbent medium from which a volatile material can evaporate as described in U.S. Pat. No. 2,626,833. In U.S. Pat. No. 855,984 a sponge is used to volatilize a perfume or disinfectant. U.S. Pat. No. 1,988,141 describes the use of a felt pad to release a perfume. These and similar articles have a very rapid release of fragrance from their matrix, and do not provide a prolonged release of fragrance.

Wood has been used to hold scent, for example, incense sticks. To release significant quantities of the scent, the wooden incense sticks are burned and the aroma is released into the environment. Allowing the incense sticks to release their scent without burning results in an inadequate scent release. Wood is not highly absorbent and therefore absorbs low amounts of scented material. Wood pulp has been used to absorb fragrance and release it, as described in U.S. Pat. No. 2,120,204. The use of wood pulp may pose problems when it is friable and cannot be made into stable articles.

Wood sticks or reeds, without a fragrance applied initially, have been used in reed diffusers. In a reed diffuser, the wood, such as two or three bamboo reeds, are placed in a container holding a scented oil. The oil wicks up the central portion of the reed and the fragrance volatilizes out the upper end of the reed. The reeds must be turned frequently so that the previously immersed end of the reed is exposed to the air outside the container. Often the reeds clog from debris or biocontaminants in the oil, and are not effective at providing long-term fragrance to an environment.

What is needed are articles that provide olfactory-active substances, and methods for making and using such articles, and compositions used for articles that provide olfactory-active substances, such as fragrance, to an environment, including articles that are durable, easily manufactured and provide a slow or controlled rate of release of the olfactory substance, such as fragrance, for many applications.

SUMMARY

The present invention is directed to methods and compositions for an article that provides an olfactory-active substance, such as a fragrance, to an environment and to methods for making and using such an article. An aspect of the invention comprises an article comprising a structural component and at least one olfactory-active substance. A structural component comprises a matrix material that is an absorbent material. In an article, the matrix material absorbs or adsorbs the at least one olfactory-active substance. The matrix material may have additives incorporated into the matrix material. A structural component may have at least a portion of the surface of the structural component covered or overlaid by a coating or a barrier. The coating or barrier may aid in the controlled release of the olfactory-active substance from structural component, and may extend the length of time that the olfactory-active substance is released from an article.

FIGURES

DETAILED DESCRIPTION

Figure 1:
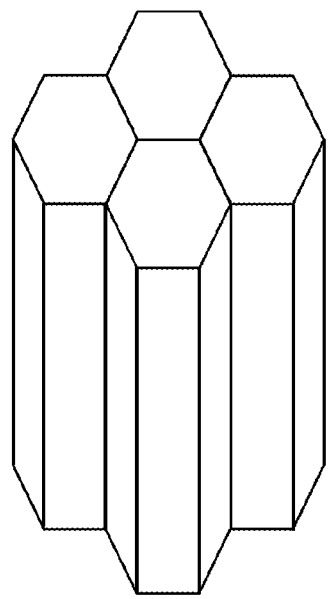
FIG. 1 is a drawing of an example of an article of the present invention.

The present invention comprises articles, methods and compositions that provide an olfactory-active substance, such as a fragrance, to an environment. The present invention comprises methods and compositions for articles that provide one or more olfactory-active substances, for example, fragrances, to an environment. An article of the present invention may comprise one or more olfactory-active substances, such as fragrance, contained in a portable, free-standing structural component. An article may be two-dimensional with varying shapes and sizes, such as flat sheet embodiments, or an article may be three-dimensional with varying shapes and sizes, such as a desired shape, a solid rod, a rod with a core, a rod with two cores, a rod with a honeycomb structure, a solid sphere, a hollow sphere, or any other geometric shape, or other possible arrangements.

An article may be provided individually or in groups of two or more, and may be held in a receptacle having apertures to allow the passage of fragrance molecules. An article may be provided in any shape, for example, as a rod or a shaped rod, such as by crimping or bending a rod, or may be assembled from a combination of articles, such as placing several small rods, each held with another rod by a holder and the articles so held provide a shape. An article may optionally further comprise dyes, coating compositions, holder elements or attachment elements.

An article of the present invention comprises a structural component which is made from a matrix material composition, and an olfactory-active substance. A structural component, may be coated, dyed, or further treated in forming an article of the present invention.

The present invention comprises compositions used in making an article. A structural component may comprise one or more matrix material compositions. A matrix material composition may comprise natural and synthetic pulp compositions, or pulp compositions combined with other products, including but not limited to paper, cellulose, cellulose acetate, pulp lap, cotton lintners, biological plant-derived materials (from living plants), synthesized pulp compositions, and mixed pulps. A matrix material composition may comprise additives, materials that provide strength, rigidity or structure to a matrix material composition. For example, a composition may comprise nanomaterials as additives. An article of the present invention may be referred to as a pulp article, indicating that the article comprises a matrix material composition which was made from a pulp composition of the present invention.

The present invention comprises methods of making the compositions, methods of making articles comprising compositions, and methods of using an article.

A matrix material composition may comprise pulp. As used herein, and as known in the art, pulp is primarily a collection of fibers with other components of the source material, wherein the fibers are derived from a natural or synthetic source material, for example, biological plants (natural) or petroleum-based synthesis products (synthetic). The pulp composition may have a moisture content. Pulp and pulp composition are used interchangeably herein. Basic steps in pulp making are well known in the art and comprise converting plant fiber or other fibers into a usable form such as chips, converting chips into fibers or pulp, optionally treating the pulp such as bleaching the pulp, washing the pulp, and forming a pulp composition. Pulp may be produced from various types of woods using any one of several pulping techniques. The pulp may be from hardwoods, softwoods, or mixtures thereof. Suitable hardwoods include, but are not limited to, aspen, birch, cottonwood, poplar, maple, and the like, and mixtures thereof. Suitable softwoods include, but are not limited to, pine (e.g., red pine, jack pine, and Southern yellow pine), spruce, balsam fir, Douglas fir, and the like, and mixtures thereof. The pulp may be a mixed-blend of wood from various species of hardwood, deciduous trees including, but not limited to, ash, aspen, beech, basswood, birch, black cherry, black walnut, butternut, buckeye, chestnut, cottonwood, dogwood, elm, eucalyptus, gmelina, hackberry, hickory, holly, locust, magnolia, maple, oak, poplar, red alder, redbud, royal paulownia, sassafras, sweetgum, sycamore, tupelo, willow, yellow-poplar, and combinations thereof. The pulp may comprise wood from various varieties of trees within the species of trees. It is contemplated that other species of hardwood or deciduous trees may be used. It is also contemplated that a single species of hardwood or deciduous trees may be used.

The pulp may comprise non-wood fibers including, but not limited to, bagasse, straw, kenaf, grasses, hemp, and combinations thereof. It is contemplated that pulp may comprise wood from hardwood or deciduous trees in combination with non-wood fibers.

Pulp may be made from recycled materials, and comprises recovering waste paper and remaking it into new products. Three categories of paper that can be used as feedstocks for making recycled paper are mill broke, pre-consumer waste, and post-consumer waste. Mill broke is paper trimmings and other paper scrap from the manufacture of paper. Pre-consumer waste is material which left the paper mill, which has been discarded before it was ready for consumer use. Post-consumer waste is material discarded after consumer use, such as old magazines, old newspapers, office waste, old telephone directories, and residential mixed paper. Paper suitable for recycling is called scrap paper. Feedstocks for pulp may comprise a range of about 100% scrap paper to 0.001% scrap paper, and may comprise mixed pulp compositions comprising virgin fibers and recycled fibers. Deinking processes may be used with recycled materials.

Methods for making pulp include (i) chemical, (ii) mechanical, (iii) thermal, and (iv) combinatorial methods. Industrial alkaline chemical pulping processes include the Kraft (or sulfate), soda, and alkaline sulfite processes. The Stone GroundWood (SGW) process involves making pulp by pressing logs and chips against an abrasive rotating surface. Another type of mechanical pulping is Refiner Mechanical Pulp (RMP) featuring atmospheric refining with no pre-treatment of wood chips.

Thermo Mechanical Pulping (TMP) is a mechanical pulping process that evolved from RMP and a high temperature process known as the Apslund process. Thermo Refiner Mechanical Pulping (TRMP) is a variation in Thermo Mechanical Pulping. In this case, the chips are preheated under pressure and refining is carried out at atmospheric pressure.

Other pulping methods include chemical treatment with thermo-mechanical pulping (CTMP), chemi-mechanical pulping (CMP), and the chemical pulping, sulfate (kraft) or sulfite processes. Pulps may be treated, for example to lighten the color of the pulp. Bleaching may use chemical products to dissolve and extract part of the lignin, or to discolor it. These chemical products include chlorine dioxide, hydrogen peroxide and ozone for chemical pulps, and hydrogen peroxide for mechanical pulps.

Electron beam processing or electron processing technology (EPT) of chemical wood pulp can be used to control pulp viscosity or degree of polymerization.

It may be desirable to generate pulps with lower overall lignin content, or no lignin content, as these pulps require less bleaching chemicals, react less with fragrances, and generate fewer pollutants, especially absorbable organic halides (AOX). Cellulose pulps having a high lignin content are referred to as "high-yield pulps," and this class of pulps includes groundwood pulps, chip-refined pulps, thermo-mechanical pulps, chemi-mechanical pulps, and semi-mechanical pulps. The fibers of the lignocellulosic material are freed at least in part mechanically and optionally also in part chemically. The mechanical defibration is effected in a grinder, a disc refiner or a screw defibrating apparatus, in which the pulp is subjected to a mild mechanical shearing force without appreciably lowering its resistance to dewatering. Fibrillation may be used increase the flexibility of the fibers and bring about the fine material characteristics of quality processed pulp.

Methods of the present invention comprise forming an article of the present invention having a structural component comprising a pulp matrix material. An example of a method for making a matrix material comprises forming a sheet of paper from pulp. After the wood chips are digested and optionally, the resultant fibers bleached, the fibers are formed into a wet-laid pulp mat. In this operation, the fibers enter a headbox where they are mixed with water and any chemicals or other materials that are added to the pulp. The fibers exit the headbox onto a moving screen, known as a wire through which the water in the web is drained both by gravity and by vacuum. This step, known in its initial stage as formation, is usually accomplished by passing an aqueous dispersion of a low concentration of pulp (e.g., 0.5% to 1% by weight solids is typical) over the wire. This wire, assisted in certain situations by vacuum or suction, increases the consistency of the mat or web to approximately 20 to 35 weight percent solids.

The mat or web is then compressed or squeezed in a "press section" to remove additional water. This is usually accomplished by felt presses, a series of rollers each having a felted band for contact with the mat or web. These presses remove additional free water and some capillary water, thus resulting in an increase in consistency of the mat or web to a range of about 30 to 60 weight percent. More or less pressing may be applied, depending on the desired product.

Following the press section, the pulp sheet is then dried in a dryer section. In the drier section, the remaining water content of the pulp sheet is reduced to obtain a pulp consistency which typically ranges between about 88 to 97 weight percent (3 to 12 weight percent moisture), more usually between 90 to 94 weight percent (6 to 10 weight percent moisture). The wet-laid cellulose pulp fibers form into a sheet and attach to each other at contact points by hydrogen bonds. This process is called wet forming.

Other methods of making pulp matrix material are known. For example, in the Fourdrinier process, a pulp matrix material is generally produced by forming a fiber mat from aqueous cellulosic slurry on a wire screen. Methods generally comprise a head box having a flow chamber upstream from the wire screen. The head box receives the aqueous cellulosic slurry and deposits the slurry onto the wire screen where a paper mat is formed. The paper mat is removed from the wire screen and further processed, including drying, to form article matrix material. Dry or wet lap processes may also be used to form pulp matrix materials.

Commercial pulps may be available in sheet form. In order to facilitate the blending of the fibers with a polymeric material, the fiber sheets may be broken down to individual fibers or small aggregates of fibers. The step of granulating may be performed using a rotary knife cutter to break up the pulp material. The granulation process may reduce the length of the fibers. A reduction in fiber length may decrease the reinforcing impact of a fiber additive.

Porosity of a matrix material may be controlled by the compactness of the fibers. Porosity of a pulp or an article of the present invention may be controlled or altered in various ways. The compactness of the fibers affects the degree in which the matrix material allows gas or liquid to pass through it. The matrix material porosity may affect other properties of the matrix material or the article made with such a matrix material, and changes in porosity may effect changes in other characteristics of the article. For example, porosity may affect uptake or load amount of olfactory-active substances, or may affect the rate of release of olfactory-active substances. Porosity of the matrix material may be affected by adding other materials, such as additives, to the pulp, as the matrix material is being formed from a pulp composition, or to a structural component made from a matrix material.

The nature of a pulp matrix material is such that the bonding of pulp fibers produces many tiny air passages throughout the pulp matrix material, which can either be completely submerged in the matrix material of a structural component, extend from the surface down into the interior of the structural component of an article, or penetrate completely through the structural component of an article.

The porosity of a pulp matrix material may be affected at any stage of the pulp matrix material production process. An increased level of fiber refining causes the fibers to bond together more strongly and tightly, making the pulp matrix material denser, reducing the network of air passages and the porosity. Surface sizing, coating, calendering or supercalendering may seal and/or compress surface fibers, reducing the porosity of the structural component.

Porosity may affect how completely and how quickly additives, olfactory-active compositions or other liquids are absorbed into a pulp matrix material, such absorption may occur primarily by capillary action. Pulp matrix material with high porosity may have increased additive absorbency.

Porosity of a pulp matrix material is measured quantitatively as either the length of time it takes for a quantity of air to pass through a sample, or the rate of the passage of air through a sample, using either a Gurley densometer (in the first case) or a Sheffield porosimeter (in the second case).

Porosity of a matrix material, a structural component or an article, may be increased or decreased by the addition of additives. Additives may be added to pulp during the pulp making process, during formation of the matrix material, during formation of the structural component from a matrix material, or at steps when an article is formed. For example, additives can be provided to pulp that are space-filling additives to make a matrix material having space-filling additives. An article is formed with a structural component made from the matrix material with space-filling additives and then is treated in such a way that the space-filling additive is destroyed or reduced in size, leaving openings or pores in the matrix material of the article, and increasing its porosity.

The overall porosity of an article may be decreased by treating at least a portion of the surface of a structural component of an article. The porosity of an article may be affected by reducing the porosity of the matrix material, reducing the porosity of the structural component, such as by coating or treating a portion of a surface of the structural component, or by coating or treating a portion of the article. Conversely, the porosity of an article may be increased.

Cellulosic matrix materials may be formed that have pores, gaps, or channels similar to those found in a flexible sponge. Such matrix materials may have functional groups, such as ion-exchange groups, chemically bonded to the cellulose. In a method, as described in GB 914421, a pre-formed flexible cellulosic sponge is modified by reaction with a reagent which introduces ion-exchange groups, such as orthophosphoric acid or sodium chloroacetate. GB 1387265 discloses ion-exchange cellulosic material prepared by reaction of cellulose with a reagent which introduces ion-exchange groups, followed by regeneration into the desired physical form, among which is sponge. GB 1226448 discloses a method of making an ion exchanger, which comprises the introduction of cross-linking residues into regenerated cellulose together with or followed by introduction of cation or anion exchange groups into the cellulose. The cellulose may be obtained from viscose. The cellulose may be used in a variety of physical forms such as rod, filament, yarn, woven cloth, flakes, beads, granules, powder, sponge, tube or sheet.

A matrix material of the present invention may comprise primary and secondary pores. The primary pores are interconnecting pores which are dimensioned so as to allow the free passage of liquids or gases throughout the matrix material. The secondary pores are provided in the walls of the primary pores. The rate of transport of liquids or gases in and out of the pores may be rapid or slow.

The production of a porous matrix material comprising interconnecting pores generally involves contacting a solution of the matrix material, such as a polymeric material, with a pore-forming agent such as a gas. Where the polymeric material is cellulose, the polymeric material is contacted with the gas either prior to, or simultaneous with, generation of the porous material. A gas or gas forming materials are introduced into the polymeric solution. Examples of gas-forming materials include solids, volatile liquids, chemical reagents, such as calcium carbonate and acid, thermally decomposable materials which will cause evolution of a gas by, for example, decomposition of bicarbonate, or biological agents, such as dextrose and yeast.

Gas-forming materials may be solid reagents such as powders, crystals, oils, waxes or ground biological tissue. The use of solids as precursors for the gaseous pore-forming agents may be suitable for the production of primary pores. A gas-forming reagent may be removed after or during the regeneration of the cellulose into solid form, the removal typically involving either treatment with an acid, an alkali, or an enzyme, the use of electromagnetic energy or solvent action.

A method of producing a porous matrix material having an interconnecting porous structure involves use of a xanthate. The size of pores produced by gas given off by the xanthate can be varied by varying the degree of substitution of the xanthate.

A method of producing a porous matrix material having an interconnecting porous structure involves the use of crystals of hydrated sodium sulfate where particles of varying sizes can again be used. Crystals of hydrated sodium sulfate having a particle size in the range from 200 to 400 microns can be used to make the interconnecting pores. Crystals of hydrated sodium sulfate having a particle size of 1500 to 3000 microns can be used. For pore sizes in the order of 100 microns other solids such as calcium carbonate may be used.

The actual volume of the primary pores (i.e., fractional voidage) is dependent on the amount of primary-pore forming agent introduced into the porous matrix material polymeric solution and may take any value up to 95% of the total void volume.

The thickness of the walls of the primary pores may depend on the quantity of primary pore forming agent which is mixed with the solution of porous matrix material polymeric material. Among other factors, the minimum wall thickness may depend on how closely the particles of the primary pore forming agent fit together. The overall amount of functional groups which can be introduced per unit volume into the porous matrix material will generally be increased as the density of the porous matrix material is increased. The thickness of the primary pore walls may be varied depending on the article to be made from the porous matrix material. It may not be possible to obtain uniform wall thicknesses within a porous matrix material. For example, a cellulosic porous matrix material may have a wall thickness ranging between 5 and 45 microns.

The secondary pores may be naturally occurring in the polymer as a result of variation in its density or may be formed by the use of a pore forming agent or agents which are generally used in conjunction with the primary pore forming agent. Typically the secondary pores are smaller than the primary pores and may be formed by any of the following methods.

A solution of the polymeric material may be mixed with a removable reagent having individual particles of a predetermined size, so as to produce a porous matrix material having a desired secondary pore structure (i.e., a structure having a pore size determined by the reagent particle size). A liquid (probably immiscible with the polymer solution) can be added to the polymer solution which upon mixing forms continual channels within the liquid polymer. Alternatively, the density of the polymer solution, such as cellulose, may be lowered by the addition of a suitable solvent so that when the cellulose is regenerated, the resulting sponge has an open pore structure. Suitable methods of removing the added gas or liquid are known. Secondary pores may be produced by contacting the polymer solution with a solid pore-forming agent.

It is recognized that the nature of a porous matrix material, including the general porous structure, may depend on a wide range of factors which influence the manufacturing system. For example, changes may be made to the concentration, degree of polymerization, or viscosity of the polymer. Agents, such as surfactants, likely to effect the secondary and primary pore structure may be added.

The porous matrix material may be used in accordance with the present invention to form a structural component of an article as described herein and which may be in the form of a block, an annulus, a continuous sheet, a rolled sheet, a disc, a tape, a rod, a pad, or other three-dimensional form, or the like.

A matrix material comprising lintners, including but not limited to, cotton, lotka or abaca, is contemplated by the present invention. The lintners may comprise from 0.1% to 99.9% by weight of the total weight of the matrix material. A matrix material comprising a synthetic pulp is also contemplated by the present invention. For example, U.S. Pat. No. 3,770,856 discloses the production of fine fibrous structures by flashing an aqueous emulsion containing a polymer and solvent from a higher pressure and temperature zone to a lower pressure and temperature zone. The resulting structure is macerated in a mixer whereby obtained are fine flat fibers in a fibrillar state of an average width of from 5 to 10 microns and length of from 3 to 5 mm. The resulting fibers can be pressed or molded to form a matrix material for use in a structural component.

Extruded synthetic pulp compositions are used to form matrix materials of the present invention. British Pat. No. 1,221,488 discloses a process for the production of yarn which involves extruding a blend of polyethylene and blowing agent so as to produce an extrudate of foamed polyethylene. The latter is drawn so that it becomes orientated essentially in the direction of extrusion. The drawn foamed polyethylene is subjected to forces such that the walls of the foam are broken down. The resulting extrudate is a three-dimensional structure of interconnected fiber elements which comprise a matrix material. U.S. Pat. No. 3,634,564 discloses a process for the manufacture of fibrillated foamed films involving mixing a thermoplastic polymer with a blowing agent and extruding the mixture into a foamed polymer film and thereafter stretching the foamed film uniaxally. The stretching at an elevated temperature causes the voids of the foam to split. These fibers may be formed, pressed, molded, melted, partially melted or treated in known methods to form matrix materials for use as structural components.

In some cases, the extrudate is orientated. Orientation refers to a process wherein the crystalline structure in polymeric materials are placed in alignment so as to produce a highly uniform structure. It is believed that orientation causes the axes of the molecules of the polymer to more generally line up in the same direction. Generally orientation is obtained by stretching (or pulling) the polymer while its temperature is below its melting point but above its transition temperature. The present invention contemplates extrudates that are not drawn or oriented and the resulting fibers may or may not be oriented in a matrix material.

U.S. Pat. No. 3,954,928 discloses a process for the preparation of fibrillated extrudate by extruding a molten thermoplastic resin containing a foaming substance through a die. The extrudate is quenched almost as it leaves the die to a temperature below the resin's glass transition temperature. The resin can be a blend of polystyrene and a polyolefin, e.g., polyethylene, but the latter is present in an amount of at most 40% and preferably 30% or less by weight based on the blend.

U.S. Pat. No. 4,210,487 discloses that a polyolefin by itself can be processed to fibers suitable for blending with cellulosic pulp to form a matrix material. A mixture of polystyrene and polyethylene or polypropylene in which the mixture contains more than 40 weight % of the polyolefin is equally suitable for blending with cellulosic pulps. U.S. Pat. No. 4,210,487 further discloses a process of preparing a synthetic pulp composition from a synthetic thermoplastic, fiber-forming polymer. The resin is extruded along with a blowing agent to form material having interconnected fibrils and fibers. The material is attenuated as it leaves the extruder die to induce formation of fibers and fibrils. The attenuation occurs while the polymer is in a molten or amorphous state. The resulting fibrillated material is then subjected to a cutting and/or shearing action which results in the foamed material breaking down into small short fibers having many attached fibrils. This synthetic fibrous material readily mixes with cellulosic pulp to allow preparation of a paper sheet having varying amounts of the desired synthetic polymer. The resulting paper, depending on the particular polymer and the amount can have properties superior to that of paper of only cellulosic pulp. The synthetic thermoplastic polymer is selected from the group consisting of polypropylene, polyethylene or a mixture of polystyrene and polypropylene or polyethylene in which the mixture contains more than 40 percent by weight of the polyolefin.

The present invention comprises compositions comprising additives. One or more additives may be added to a matrix material composition, such as a pulp. Pulps may comprise additives that are added during production of the pulp, and/or during formation of a matrix material, or during formation of a structural component of an article, to confer one or more special characteristics. For example, the addition of mineral fillers such as kaolin, titanium oxide, talc, calcium carbonate, may aid in printability, opaqueness and dimensional stability of matrix material and/or a structural component. Additives may be incorporated in a pulp composition, in the matrix material of an article as it is being formed, in the article after formation or in an olfactory-active substance composition.

An example of an additive is a starch. Starch compounds may be added in the matrix material itself, or may be used to adhere one layer of a paper matrix material to another layer of paper in a rolling process to produce a structural component comprising a rolled continuous paper rod. The starch compounds may be used as control release elements. Both natural unmodified starch and modified starch can be used. Any starch appropriate for use in papermaking may be used including but not limited to, dextrin, as well as combinations of starch types, dextrin types and combinations of starches and dextrins. Also, maltodextrins and other forms of carbohydrates can be used as the starch component. Unmodified starch is a commodity chemical produced from the root, stem or fruit from a number of plants. It is a high molecular weight carbohydrate polymer which is comprised of linear and branched polysaccharide polymers and it may have a moisture content from about 8% to about 20%, most commonly from about 11% to about 13%. Starches such as those derived from corn, wheat, barley, tapioca, rice, potato and/or other suitable plant source, and the like can be used, as well as hybrids. Blends of starches from various sources also can be used. Pearl starches and powdered starches may be used.

Modified starch can be mechanically, chemically or heat modified. Modified starches have different properties than unmodified starch, including differences in solubility, film forming, whiteness, gel strength, viscosity stability, adhesivity, resistance to shear and resistance to freeze-thaw degradation. Starches derived from other genetic forms of corn, such as high amylose and waxy corn, as well as sorghum varieties, would also be suitable. Chemically modified starches include modified oxidized starch such as hypochlorite-oxidized starch, acid thinned starches, cross-bonded starch, etherified starches, esterified-starches and others which have reduced molecular weight, high fluidity and/or functional subgroups. Examples of chemically modified starches that are commercially available are SUREBOND™, Industrial Corn Starch, or STABLEBOND™. Industrial Corn Starch available from Corn Products, FOXHEAD™. Cationic Starches are available from Corn Products and Corn Products' oxidized starch.

Additives may comprise nanofibers. Nanofiber is a broad phrase generally referring to a fiber with a diameter less than 1 micron. Examples include, but are not limited to, glass fibers in the sub-micron range, polymeric meltblown fibers, 0.25 micron diameter electrospun nanofibers commercially available nanofibers and nanofiber webs.

Nanofibers may be organic or inorganic materials including, but not limited to, polymers, engineered resins, ceramics, cellulose, rayon, glass, metal, activated alumina, carbon or activated carbon, silica, zeolites, or combinations thereof. Combinations of organic and inorganic fibers and/or whiskers are contemplated and within the scope of the invention as for example, glass, ceramic, or metal fibers and polymeric fibers may be used together.

Nanofibers, comprising nanofibers or microfibrils made from cellulose, may be added to a pulp composition used as a matrix material of the present invention. A plant cell wall is in part stiffened by cellulose microfibrils. In general, cellulose fibers are 30 mm wide and about 2-3 mm long, and are made of nanometer scale microfibrils which are typically 4 nm wide and about 100-200 nm long. As used herein "microfibrillated cellulose" or "cellulose nanofibers" or cellulose microfibrils are used interchangeably and are understood by those skilled in the art to mean very small fibers derived from cellulose. Microfibrillated cellulose (MCF) is isolated and purified cellulose fibers recovered from a cellulose source in a process which results in cellulose filamentous structures that are nanoscale size.

MCF was developed in the 1980s and is a form of expanded high-volume cellulose, moderately degraded and greatly expanded in surface areas that may be obtained by a homogenization process. MCF nanofibers may be used to add strength and other properties to pulp products. Conventionally, MCF is obtained through mechanical treatment of pulp fiber by refining, followed by high pressure homogenization. Refining produces external fibrillation of fibers by gradually peeling off the external cell wall layers (P and S1 layers) and exposing the S2 layer. Internal fibrillation loosens the fiber wall. Refining is common in the paper industry and is accomplished using a refiner. For example, in a disk refiner, a dilute fiber suspension is forced through a gap between the rotor and stator disks and the fibers are subjected to repeated cyclic mechanical stresses. The treated fibers are then homogenized by pumping the slurry of cellulose fibers through a spring-loaded valve assembly. As the valve opens and closes rapidly, the fibers are subjected to a large pressure drop with shearing and impact forces which promotes a high degree of microfibrillation of the cellulose fibers, resulting in MCF. Enzymes may be used to pretreat the pulp fiber. Post treatments may include grinding. Grinding comprises passing the homogenized fiber solution to a grinder, made from a static grind stone and a rotating grind stone. See for example, U.S. Pat. Nos. 6,214,163 and 6,183,596.

MCF has been characterized by microscopy, such as scanning and transmission electron microscopy and atomic force microscopy, to comprise interconnected web-like structures of tiny fibrils and microfibril bundles, and diameters of the fibers range from 1 to 100 nm. A substantial part of the fibrils in MCF are relatively uniform in size. The length may by from about 100 nm to more than 1 mm. The surface area to volume of MCF is increased compared to the original pulp fibers.

In general, MCF is a form of expanded high volume cellulose in which cellulose fibers are opened up and unraveled to expose smaller fibrils and microfibrils. MCF comprises nanostructures that provide high stiffness and strength, crystals with self-organizing effects, and hydroxyl groups at the surface, which provide reaction sites for modification. When MCF is added to a pulp, the pulp product has improved strength, including the tensile strength, burst strength and tear strength, and other characteristics such as density, smoothness and may increase the air permeability of the pulp product, such as an article of the present invention. Matrix materials of the present invention comprise MCF, and, similar to pulp compositions containing MCF, show increased retention and absorption of liquids, such as dyes and olfactory-active compositions.

MCF may be added to coating materials which are used to coat pulp matrix materials, and may be used in an article of the present invention. MCF added to a coating material may aid in improving the printability of the coated surface and may aid in increasing the viscosity of the coating materials to reduce streaking. MCF may also be used as a carrier for other substances, such as dyes, pigments or olfactory-active substances.

MCF properties include fine scale-high surface area, high crystalline characteristics, increased stiffness and strength added to pulp products comprising MCF, and hydroxyl groups for chemical and physical modifications such as are known to those skilled in the art. Commercially available MCF may be used as an additive for matrix materials of the present invention, made for example from hardwood, pulp or from softwood. A commercial source for MCF is MCF-lyocell microfibrillated fiber from Engineered Fibers Technology, LLC, which has a high number average of microfibrils with diameter of 0.1-0.25 mm. MCF may be further refined using for example, Valley Beater equipment.

When adding MCF to a pulp solution, MCF may comprise from 0.001% to 50% of the pulp composition, from 0.01% to 50%, from 0.1% to 50%, from 1.0% to 50%, from 10% to 50%, from 0.01% to 45%, from 0.01% to 40%, from 0.01% to 30%, from 0.01% to 20%, from 0.01% to 10%, from 0.1% to 10%, from 1.0% to 10%, from 0.001% to 10%, from 0.01% to 1%, from 0.001% to 1.0%, from 5% to 20%, and all ranges thereinbetween are included. Addition of MCF to a pulp results in a pulp matrix material, that, when compared to a pulp matrix material without MCF, has different characteristics, including but not limited to, improved tensile strength, improved water absorption capacity-Cobb value, and improved vapor transfer ability (MTVR).

An additive of the present invention comprises glue, an adherent material. Glues are known to those skilled in the art, and choosing a glue with the desired adherent properties can be determined by those skilled in the art. A glue may or may not also comprise an olfactory-active substance. A glue may act as an inhibitor of release of an olfactory-active composition, thus lengthening the time an article releases the olfactory-active composition. A glue may be applied in a uniform or non-uniform manner to a matrix material. For example, in a rod shaped structural component made from a wound paper matrix, whether spiral wound or not, a glue may be used to adhere one or more layers of the paper together. Glue may be applied as dots on one or more layers or plys and the glue may serve as a spacer between the plys to create voids between the layers.

An aspect of the present invention comprises adding one or more olfactory-active substances to one or more of a pulp, to a matrix material made from pulp, to the structural component made from the matrix material, or to each of a pulp, the matrix material, and the structural component. Olfactory-active substances include but are not limited to, fragrances, repellants, odor-eliminating compounds, aromatherapy compounds, natural oils, water-based scents, odor neutralizing compounds, and cyclodextrins. As used herein, "olfactory-active substance" refers to any compound, mixture or suspension of compounds that are odorous, or compounds mixture or suspension of compounds that cancel or neutralize odorous compounds, such as any compound or combination of compounds that would produce a positive or negative olfactory sense response in a living being that is capable of responding to olfactory compounds, or that reduces or eliminates such olfactory responses. A fragrance of the present invention comprises an aroma or odorous compound, mixture or suspension of compounds that is capable of producing an olfactory response in a living being capable of responding to olfactory compounds, and may be referred to herein as odorant, aroma, or fragrance. An olfactory-active composition as used herein comprises one or more olfactory-active substances and is generally a composition that has a smell or odor, which may be volatile, which may be transported to the olfactory system of a human or animal, and is generally provided in a sufficiently high concentration so that it will interact with one or more olfactory receptors. A fragrance composition may include one or more than one of the fragrance characteristics, including topnotes, midnotes or heart, and the drydown or base notes. An olfactory composition may comprise other diluents or additives, such as solvents or preservatives.

Synthetic wood materials, such as cellulosic-reinforced plastic composites are contemplated by the present invention. Cellulosic refers to cellulose acetates and cellulose acetate esters and includes, but is not limited to, cellulose acetate, cellulose acetate propionate, and cellulose acetate butyrate. Cellulose acetate esters include, but are not limited to, cellulose diacetate and cellulose triacetates. The term cellulosic also includes all hydrates of cellulosics (e.g., anhydrous cellulose acetate, cellulose acetate monohydrate, cellulose acetate dihydrate, cellulose acetate trihydrate, and cellulose acetate tetrahydrate) as well as anhydrous forms of cellulosics. Suitable purified cellulosic pulps include Ultranier-J, Rayfloc-J-LD, Porosanier-J-HP, Ethenier-F-UHV, Sulfatate-H-J-HD and Placetate-F, each of which are available from Rayonier, Specialty Pulp Products (Jessup, Ga. and Fernandina Beach, Fla.). These cellulosic pulps have an alpha-cellulose purity of 95% or greater with the exception of Rayfloc-J (about 86% alpha-cellulose content). All are softwood pulps with the exception of Sulfatate-H-J which is manufactured.

Biomass plastics are contemplated by the present invention and are derived from renewable plant resources such as cornstarch, cellulose, and soy bean oil, rather than limited fossil resources, such as petroleum. Renewable resources are a more viable and promising alternative for the plastics industry. Cellulose acetate is one of the most important synthetic organic esters because it is made from cellulose, the most abundant biopolymer on earth. Cellulose acetate is biodegradable by certain microorganisms, and is made from renewable resources, such as wood pulp, agricultural refuse or cotton fiber. Cellulose acetate can be used as a film or as a fiber, and the fibers can be woven into fabric which resists mildew and mold and may be formed into matrix materials. In an embodiment of the present invention, cellulose acetate is the matrix material that is used to form a fiber bundle to make a structural component, for example, a cylinder. The cylinder may be solid or have a hollow axis. The cellulose acetate cylinder may be treated with coatings, or may have a coating or barrier, such as a paper wrapping around the outer surface, to aid in controlled release of one or more olfactory-active compositions.

An exemplary embodiment of a cellulosic-reinforced plastic composition exhibits excellent physical properties and moldability characteristics. An exemplary embodiment of a cellulosic composite material composition is generally comprised of a plastic resin and a cellulosic filler material in a range of particular proportions, and may be produced in either a solid or a foamed form. Moreover, the ingredients of the composite may be made from recycled or virgin materials.

Plastic resins and cellulosic fillers may be combined. For example, an article of the present invention may comprise a structural component comprised of a matrix material of a cellulosic pulp, such as cellulose acetate and a resin, and may be formed into a suitable shape, for example a rod, around which a paper is placed. Suitable thermoplastic resins may include: multi-layer films; high-density polyethylene (HDPE); low-density polyethylene (LDPE); polyvinyl chloride (PVC); chlorinated polyvinyl chloride (CPVC); semi-rigid polyvinyl chloride (S-RPVC); polypropylene (PP); ethyl-vinyl acetate; acrylonitrile butadiene styrene (ABS); polystyrene; and other similar or suitable polymers and copolymers. Optional thermoset materials may include: polyurethanes (e.g., isocyanates); phenolic resins; epoxy resins; unsaturated polyester, and other similar or suitable thermoset materials. Cellulosic materials acceptable for use in such a composite may include: sawdust; newspapers; alfalfa; wheat pulp; wood chips; wood fibers; wood particles; ground wood; wood flour; wood flakes; wood veneers; wood laminates; paper, cardboard; straw; cotton; rice hulls; coconut shells; corn cobs; peanut shells; bagasse; plant fibers; bamboo fiber, palm fiber, kenaf; jute; flax; and other similar or suitable cellulosic materials.

Many other materials may also be added to a composite to improve its properties or improve processing. These materials may include inorganic fillers, cross-linking agents, blowing agents, foaming agents, foam modifiers, lubricants, stabilizers, accelerators, inhibitors, enhancers, compatibilizers, thermosetting agents, process aids, weathering additives, rubber, colorants, mildew inhibitors, and other similar or suitable additives.

Methods of the present invention comprise making a pulp composition with a plastic resin, cellulosic filler material such as cellulose acetate, and other optional materials that may be caused to interact and form a matrix material composition. For example, a proper ratio of each of the components may be fed via a separate hopper or similar article into a mold or molding machine, e.g., an extrusion system, during the molding operation. Alternatively, the plastic resin and optional materials may be pre-mixed. Separate hoppers or a similar article may then be used to introduce the pre-mixed materials and cellulosic filler material into a mold or molding machine during the molding operation. Another method mixes the cellulosic filler with the plastic resin (plus some or all of any optional additives, if desired) prior to introducing the mixture to the mold or molding machine. Still another method allows for proper ratios of each of a thermoplastic resin, the cellulosic filler material, and the other optional materials to be fed into a compounder. The compounder is then used to combine and melt the individual components into a pelletized feedstock, which may then be cooled and stored for later use in a molding machine. The composition produced by the compounder does not, however, have to be pelletized and stored. The composite melt may alternatively be transported from the compounder directly to an extruder or other molding machine for immediate use.

Yet another method provides for the plastic resin, the cellulosic filler material, and some or all of the other optional materials to be combined in a mixer or blender. Although the blender or mixer may be heated, the components may remain unmelted during mixing. The unmelted, mixed material may then be stored for later use, or immediately transferred to a dryer to lower the moisture content of the cellulosic filler material. After drying, the unmelted, mixed material is preferably fed to a molding machine connected to the dryer, or may be placed in a compression mold. Other components may be added to the mixed, dried material at the molding machine. Furthermore, each of the aforementioned manufacturing methods may be varied.

Pulp compositions, such as cellulosic-reinforced plastic compositions and other pulp compositions disclosed herein may be used to produce matrix materials, structural components and articles by any of the traditional molding means, including, but not limited to, extrusion, compression molding, and injection molding. A profile die may be utilized during extrusion to shape a pulp composition as desired. A packer die may be used to further compress a pulp composition and improve the bonding of the pulp composition components. Compression molding of a pulp matrix material composition may be achieved by placing a dry-blended or pelletized form of a pulp matrix material composition into a compression mold and compressing the material under sufficient heat and pressure. Regarding compression molding, it has also been found that a variety of secondary sheet materials may be bonded to the surface of a pulp matrix material composition, either during the compression molding process, or afterwards by using certain adhesives or compatibilizers. Similarly, structural components or articles may also be produced by traditional injection molding means, utilizing molds and molding equipment designed for the properties and characteristics of a pulp matrix material composition.

An article of the present invention comprises a structural component comprising one or more olfactory-active compositions. A structural component may be made of pulp or any matrix material that is capable of releasably retaining one or more olfactory-active compositions. As used herein, releasably retained means that a compound or composition is maintained in or on a material, as in retained, and is capable of moving from one area of the material to another area of the material, or is capable of exiting the material. All or a portion of an olfactory-active composition may be releasably retained by a matrix material or a structural component. For example, an olfactory-active composition may be absorbed by the matrix material or adsorbed to a matrix material, and the olfactory-active composition is said to reside or be present in the matrix material, and under certain conditions or as a factor of time, all or a portion of the olfactory-active may move within the matrix material or exit the matrix material. A structural component may participate in or control the release of all or a portion of one or more olfactory compositions to the surrounding environment. A structural component may comprise a plastic material, such as a porous plastic that is resistant to an olfactory-active composition. The plastic material may form a container in which a gel matrix material is provided and the gel matrix material may comprise an olfactory-active composition. The olfactory-active composition may be released by diffusion from the gel matrix material through the plastic, such as through pores in the plastic, or through an area of the plastic container in which an opening is provided.

An article of the present invention comprises a structural component made from a matrix material and an olfactory-active composition. An article of the present invention may comprise a matrix material comprising an olfactory-active composition that was added directly to the matrix material, prior to formation of the matrix material into a structural component. An article of the present invention may comprise a matrix material formed into a structural component and after formation of the structural component, an olfactory-active composition is added. A matrix material may be a pulp composition.

An article of the present invention comprises a structural component comprising a matrix material comprising a spiral wound paper. The spiral winding process allows for the paper to be the same or different for each layer formed by winding the paper one complete revolution around the axis of the structural component. For example, a structural component may comprise a rod shape, formed by winding the matrix material, a paper matrix, around a vertical axis, so that a rod, having a length longer than its diameter, is formed. Each layer formed by the complete revolution of the paper matrix around the axis may be referred to as a ply. For example, a 10 ply rod may have from one to ten different characteristics for each ply of the rod. Characteristics may include those described herein for matrix material, and include, but are not limited to, absorbance, tensile strength density, pH, porosity, and polarity of the matrix material, and the type of paper or matrix composition.

An aspect of an article of the present invention comprises a matrix material comprising a perforated paper matrix material, with holes formed through the paper matrix. A hole so formed may be "clean" or free of chads, or may have the removed material, which by its removal formed the hole, referred to herein as a chad, attached in some manner with the hole. If chads are maintained with the matrix, some or all of the chads may be present, and some or all of the chads may be attached to their source. Some or all of the chads may be free from the source point of the chad and may serve as spacers, for example, between plys of a spiral wound paper matrix rod. Chads may be removed from the paper matrix material prior to forming a rod, for example, by a spiral winding process.

Perforations in a paper matrix, to form holes, may be made so that each ply of a structural component, such as a rod, has the same or different numbers of perforations as one or more other plys, or perforations in different or the same pattern as one or more plys of the structural component. Perforations comprise holes having a diameter of a desired size, for example, from about 50 microns to about 400 microns, from about 300 microns to about 1000 microns, from about 50 microns to about 100 microns, from about 50 microns to about 1000 microns, from about 50 microns to about 500 microns, from about 50 microns to about 300 microns, from about 50 microns to about 200 microns, from about 500 microns to about 1000 microns, from about 500 microns to about 600 microns, from about 500 microns to about 700 microns, from about 500 microns to about 800 microns, and all ranges therein between. The holes may be of a uniform size, in that all perforations made are uniform in diameter, for example, about 300 microns, or the diameters may be arranged in particular patterns of differing diameter perforations, or the diameters may be random.

There may be the same or differing numbers of holes per square inch of a ply. For example, a ply may have from 100 to 1000 holes per square inch, which may be in a particular pattern or randomly created in the matrix material. The perforations may be made in a matrix material, for example, a paper, by processes known to those skilled in the art and include, but are not limited to, mechanical punch, laser created, and electrostatic perforations. For example, with a paper matrix material shaped in a long rectangle, two dimensional form, the perforations may be zone punched, such as forming a pattern or random punching from the beginning edge of the short side of the rectangle to the ending edge of the paper rectangle, or from one side the long side of the rectangle to the other side for the complete paper, or in sections throughout the length of the paper rectangle.

An article of the present invention comprise a structural component made from a paper matrix material, wherein the structural component is made by spiral winding of the paper to form a rod, wherein the length of the rod is larger than the diameter of the rod. For example, the rod has 20 plys. The innermost 1-4 plys and the outermost 1-4 plys are less absorbent than the other plys of the rod. For example, the innermost and outermost plys may be free from perforations, may be made from a less absorbent matrix, may be coated with a material to make the ply less absorbent, may have additives that reduce absorbency, and/or the paper may be treated to make it less absorbent. The plys between the innermost and outermost plys are more absorbent, which may result from perforations, may have chads, may be made from a more absorbent matrix, may not be coated with a material, may have additives that enhance absorbency, and/or the paper may be treated to make it more absorbent. Each of the absorbent plys may have the same absorbency or may be different from each other, or one or more plys may have the same or different absorbency. For example, the between layers, for example, plys 2-5 to 16-19, may have from 100 to 1000 perforations per square inch. Groups of plys may have the same absorbency. A gradient of absorbency may be formed by the plys such that from the inner plys to the outer plys the absorbency increases, or from the inner plys to the outer plys, the absorbency decreases. The plys may be arranged as described herein for any particular characteristic, and are not limited to only one characteristic, but may be arranged according to several characteristic. Absorbency is described herein for convenience and is not to be interpreted as limiting the invention. Those skilled in the art will understand that one or more characteristics may be varied or remain the same for the plys.

Though not wishing to be bound by any particular theory, it is believed that in a structural component wherein porosity is altered by providing the same or differing perforations, the fragrance added to the structural component may remain in a liquid state. The liquid state may be found in the perforations of the matrix or in spaces made between plys, such as by chads or other spacers. Spacers may be made by fibers within a matrix or other materials that create a raised surface in areas of the matrix. As the fragrance is in a liquid form, it will wick to the surface of the structural component and be released, and thus detected in the outer environment.

An article may be manufactured by combining matrix material or a structural component with an olfactory-active composition by placing the matrix material or structural component in intimate contact, a period of time, an interaction time, with an olfactory-active composition. The olfactory-active composition may be in any physical state, such as liquid, solid, gel, or gas. For convenience, a liquid olfactory-active composition is described, but this is not intended to be limiting. The interaction time may depend on the concentration or type of olfactory-active composition applied to the structural component, or how strong or intense of an olfactory-active composition release desired, and/or the type of matrix material. For example, a rolled paper rod structural component may be saturated with a liquid fragrance composition comprising approximately one (1) to three (3) grams of one or more pure fragrances and the saturation time (interaction time) may range from less than one minute to a several hours, to several days. A matrix material or structural component may be pre-treated prior to exposure to an olfactory-active composition. For example, a structural component may be placed in a drying oven to remove any residual moisture. Further method steps comprise pressure treating or vacuum treatments of the matrix material or structural component. After treatment, the article may be dried, for example by rubbing or patting dry, or other methods known for drying a surface. Drying steps may be used before or after other steps described herein.

An article of the present invention may comprise a structural component and an olfactory-active composition comprising a fragrance composition that is a pure fragrance as is understood in the perfumery industry. A pure fragrance may be 40% to 50% an essential oil. A structural component may comprise a matrix material of food grade paper rolled into a wound paper rod. For example, a 5.5 inch length wound paper rod with a $15/64$ths diameter, may have a void volume of from about 2 to about 5 g/cm$^3$, and approximately 0.5 to 5 grams of a fragrance composition, 0.5 to 4 grams, 0.5 to 3 grams, 0.5 to 2 grams, 1.5 to 5 grams, 1.5 to 4 grams, 0.5 to 3 grams, 0.5 to 2 grams, 0.5 to 1 grams, 1 to 5 grams, 2 to 4 grams, 3 to 5 grams or 2 to 3 grams of a fragrance composition, may be absorbed by the rod. For a 12 inch length wound paper rod with a $15/16$ths diameter, approximately 0.5 to 5 grams of a fragrance composition, 0.5 to 4 grams, 0.5 to 3 grams, 0.5 to 2 grams, 1 to 5 grams, 2 to 5 grams, 3 to 5 grams, 3 to 4 grams, 4 to 5 grams of a fragrance composition, may be absorbed by the rod. The amount of fragrance absorbed may depend on the matrix material, the length of time of exposure of the fragrance composition to the matrix material, the density of the fragrance, the solvents of the fragrance, the porosity of the matrix material, the method of forming the matrix material into a structural component, and additives, coatings or treatments made to the matrix material, the structural component or the article. Such parameters may be determined by those skilled in the art.

In the present invention, a fragrance composition is provided to a matrix material to provide a load of fragrance of at least 70%, at least 75%, at least 80%, at least 85%, or at least 90%, load by weight of fragrance to matrix material weight. The present invention comprises fragrance article having at least 70% load factor of fragrance compounds. It is known that the load of scented candles is 5-7%, air fresheners such as paper shaped like little trees have a load factor of 40%, and gel fragrance article are 80-85%. For example, an article comprising a structural component of a rod of rolled paper matrix material may have a load of 85%. For example, a 5.5 inch rolled paper rod may have 1.6 g of a pure fragrance composition per rod, using a method of manufacture disclosed herein.

When using a matrix material of the present invention having a fragrance load factor of at least 70%, under testing and controlled conditions, the fragrance is released from the article for more than about 10 days. A rolled paper rod may show a rapid, continuous release of fragrance for the first ten days, and as fragrance is transmitted from underlying layers to the outer layer, the fragrance is released at slower rate until the fragrance is no longer detectable. For example, an article of the present invention may release at least about 30% by weight of the fragrance compound/composition within the first 30 days of exposure to the ambient air. Alternatively, an article may release a portion of the fragrance in a short amount of time, and thereafter release fragrance in a steady state.

An article of the present invention may comprise luminescent compounds. Such compounds may be added directly to a matrix material or may be in an interior compartment, inside in a plastic structure that surrounds a portion of a structural component, or as a coating on a portion of a structural component. For example, a luminol gel may be placed within a core of a rod-shaped structural component. The luminol (3-aminophthalhydrazide or 5-amino-2,3-dihydro-1,4-phthalazinedione) is activated by addition of a mild oxidizing agent, for example, by bending an article containing luminol slightly to break a capsule containing a mild oxidizing agent, such as 0.3% hydrogen peroxide. The article then emits the cool light provided by the chemiluminescence of luminol along with one or more olfactory substances.

An aspect of the invention comprises providing an article as described herein which further comprises flavor compounds, which may be incorporated into or replace one or more olfactory-active compositions. Flavor compounds may be provided in compositions comprising solvents or diluents or other additives.

A structural component may be formed into any shape desired for a particular application. Once the matrix material is formed or made into the structural component, the structural component may be formed into a desired shape. For example, the structural component may be formed into two dimensional shapes such as sheets, disks, circles, triangles, polygons, rectangles, or patterned formats. The two-dimensional shapes may have differing sizes. The structural component may be formed into three dimensional shapes have differing sizes. The three-dimensional shapes may be solid or may comprise a compartment. The three-dimensional shapes may be hollow. For example, suitable three-dimensional shapes includes, but are not limited to, solid or hollow axis rods having various sorts of circumferences like circular, hexagonal, pentagonal, triangular, etc., balls, pellets, and other desired likeness. For example, an aspect of the present invention comprises rod-shaped structural components formed from a matrix material of paper that is wound around a central axis to form a tightly wound paper rod. A rod may be of any desired length and/or shape depending upon the application.

The structural component may be formed by any of the traditional molding means, including, but not limited to, extrusion, compression molding, and injection molding of the matrix material, for example, a pulp composition. A profile die may be utilized during extrusion to shape the matrix material as desired. A packer die may be used to further compress the matrix material and improve the bonding of the individual material components. Compression molding of the matrix material may be achieved by placing a dry-blended or pelletized form of the composition into a compression mold and compressing the matrix material under sufficient heat and pressure. Regarding compression molding, it has also been found that a variety of secondary sheet materials may be bonded to the surface of the matrix material, either during the compression molding process, or afterwards by using certain adhesives or compatibilizers. Similarly, articles may also be produced by traditional injection molding means, utilizing molds and molding equipment designed for the properties.

A structural component or a matrix material may be made using an electrospinning process. Electrospinning uses an electric field to draw a solution from the tip of a capillary to a collector. A voltage is applied to the solution, which causes a jet of the solution to be drawn toward a grounded collector. The fine jets dry to form fibers, which can be collected, for example, on a web.

An aspect of the present invention comprises a rod-shaped structural component wherein the interior of the rod is hollow. For example, in a wound paper rod, the wound paper forms an open area throughout the axis of the wound paper rod. The matrix material forms a walled structure encompassing a compartment through the longitudinal length of the rod. Alternatively, a pulp composition, matrix material, may be formed into a hollow rod in which the central axis encompasses a compartment through the longitudinal length of the article. The compartment, referred to as an interior compartment, is open to the exterior of the rod at each end of the rod. Also contemplated in the present invention are rods, made by any method known, which do not have a hollow central axis.

The interior compartment may comprise an olfactory-active composition, an olfactory-active composition gel, or other compositions. For example, the interior compartment may be filled with compounds that create an exothermic reaction. The exothermic reaction heats an olfactory-active composition in the matrix material and enhances the release rate of the olfactory-active composition. Exothermic reactions are known to those skilled in the art. For example, calcium oxide (quicklime) reacts with water to release heat. A small container of water is provided within the interior compartment of the matrix material. A user can pierce the water container, or break it open by bending the rod slightly, releasing the water to react with the calcium oxide. A similar reaction may be made with copper sulfate and zinc, anhydrous calcium chloride and water, acid and base neutralization reactions, such as sodium bicarbonate and any weak acid, for example acetic acid, and oxidation or polymerization reactions that yield heat. The open ends of the interior compartment may be capped, crimped or closed, or sealed in any manner, so as to retain the materials within the interior compartment.

Exothermic reactions may be provided by the reaction of a compound in an olfactory-active composition that reacts with another compound incorporated throughout the matrix material. For example, sodium bicarbonate particles are incorporated into the matrix material, for example sprinkled onto paper as it is rolled into a paper rod and creating an interior compartment. The olfactory-active composition is added to the rolled paper rod by inserting the olfactory-active composition into the interior compartment. As the olfactory-active composition passes from the interior compartment into and through the rolled paper matrix, a reactant in the olfactory-active composition, such as an acid, reacts with the sodium bicarbonate and produces heat. The heat produced changes the movement of the olfactory-active composition and its release into the environment.

An interior compartment may contain an olfactory-active composition, such as a fragrance, that is in a liquid or gel state and fills at least a portion of the interior compartment. The olfactory-active composition may exit the compartment through the walls forming the interior compartment and/or may exit through the material sealing the formerly open ends of the interior compartment.

A structural component may be made with a honeycomb design as exemplified in FIG. 1. One or more of the interior chambers formed by the honeycomb may be filled with materials such as gels, fragrance compounds, olfactory-active compositions or other materials, or may be empty or hollow. The honeycomb structure may be made of one material or may be made of more than one material, and may or may not be coated.

Figure 2:
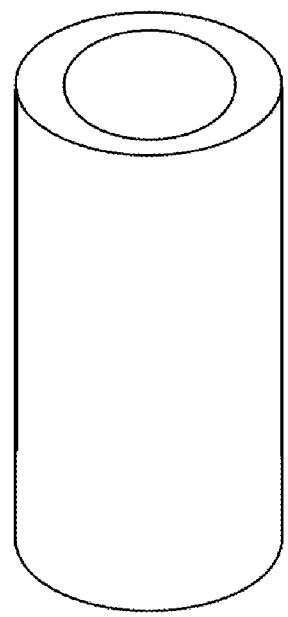
FIG. 2 is a drawing of an example of an article of the present invention.

A structural component may be made with a multi-core design as shown in FIG. 2. For example, a core of material forms the central axis of a rod shaped structural component. Another type of material surrounds the core material, as is shown in FIG. 2. Aspects of the invention comprise multi-core structural components, wherein one or more types of material, in different layers, surround the core material. The core material may be made from a single matrix composition, such as a pulp and nanofiber composition, or may be made from a combination of matrix compositions. One or more of the cores (or layers of the structural component) may comprise an olfactory-active substance, which may be the same or different in different cores or layers. Having different layers or cores of a structural component may aid in control release of one or more olfactory-active substances. Additives may be provided in the compositions forming the one or more layers or cores of a structural component.

An article of the present invention may comprise a structural component comprising a core made of a matrix material that is different from the matrix surrounding the core. For example, the structural component may comprise a core that is a sponge and the surrounding material may be made of a paper or pulp matrix described herein. Thus the article has a dual matrix material structural component. For example, the structural component may have a rod shape, with the axis of the rod formed by a core comprising a sponge matrix, and the surrounding material comprising a paper matrix applied by a spiral winding process around the core. The olfactory-active composition may be the same or different in the core and the surrounding material. The core matrix material may form the majority of the rod with a smaller amount of the surrounding material forming an outer shell around the core. For example, the core may be a liquid, gel, sponge, pulp matrix or any matrix that serves as an olfactory-active composition reservoir, and the surrounding material may serve a control release function for the olfactory-active composition. For example, the outer surrounding matrix material may be a spiral wound paper having plys with the same or different absorbency, or other characteristics, that may allow for the controlled release of the olfactory-active composition from the core.

A matrix material is the material that makes up the structural component of an article. An example of a matrix material is a pulp composition, which may or may not comprise additives. The matrix material may have varying characteristics including, but not limited to, base sheet physical properties, mechanical properties, bulk properties, color, and special features. Basis weight, thickness, width, and length are important physical properties to consider. Mechanical properties include both tensile strength and tear strength. Dielectric strength, electrical resistivity, thermal conductivity, and maximum use temperature are examples of bulk properties. The color may be determined by the position in a three-dimensional coordinate system in which one axis is the paper's brightness from 0 to 100%, another axis is the green/red direction, and the third axis is the blue/yellow direction. Brightness, opacity, and clarity are characteristics. Articles may be designed to resist flame, smoke, chemicals, ultraviolet (UV) light, or be hydrophilic, hydrophobic, recyclable, or tamper-evident. A paper usable in an article of the present invention comprises a low acid or acid free paper. Acid-free paper is paper that has a neutral or basic pH (7 or slightly greater). It can be made from any cellulose fiber as long as the active acid pulp is eliminated during processing. It may also be lignin- and sulfur-free. A paper that may be used in an article of the present invention comprising a rolled paper rod comprises an uncoated free sheet, a basis weight #24, with a 17" by 22" basis, as is known in the paper industry. Bond paper may be used that has an alkaline pH.

Examples of matrix material contemplated by the present invention include paper, laminated papers, rolled paper, compressed paper, plastics, cellulose acetate, cellulose materials such as methylcellulose or carboxymethylcellulose formed into a shape, cardboard, particle board, pressed wood, wood, fabric, woven or nonwoven fabrics, fibers from natural or synthetic sources, bamboo, recycled materials, manila hemp, carboxymethylcellulose, cellulose gums, hydrolyzed acrylonitrile graft copolymer, neutralized starch-acrylic acid graft copolymer, acrylamide copolymer, modified crosslinked polyvinyl alcohol, neutralized self-crosslinking polyacrylic acid, crosslinked polyacrylate salts, neutralized crosslinked isobutylene-maleic anhydride copolymers, or salts or mixtures thereof.

A matrix material may be made of fibers and other compounds or compositions. For example, a matrix material may comprise paper fibers and absorbent compounds. For example, a matrix material comprising 25-30% calcium carbonate may have improved absorbency capabilities. The present invention comprises an article made with a matrix material that is substantially free of calcium carbonate. For example, the matrix material may have less than 10% calcium carbonate, less than 5% calcium carbonate, less than 1% calcium carbonate, less than 0.10% calcium carbonate, less than 0.010% calcium carbonate, to substantially 0% calcium carbonate.

An example of a matrix material comprises a functional wicking material comprising a binder fiber adhered to a hydrophilic functional fiber, wherein the binder fiber is a staple bicomponent or monocomponent fiber oriented in substantially the same direction as the hydrophilic fiber. Examples of monocomponent binder fibers include, but are not limited to, PE, PP, PS, nylon-6, nylon-6,6, nylon-12, copolyamides, PET, PBT, and CoPET. Preferred bicomponent binder fibers made of polyethylene/PET, polypropylene/PET, or CoPET/PET. Monocomponent binder fibers are PE, PP, or PET. Examples of suitable hydrophilic functional fibers include, but are not limited to, high absorbent rayon, Lyocel or Tencel, hydrophilic nylon, hydrophilic acrylic fibers, and cellulosic based high absorbent fibers. A functional wicking matrix material comprises from about 1 to about 98 weight percent, from about 5 to about 95 weight percent, or from about 5 to about 50 weight percent of binder fiber. A wicking matrix material comprises from about 5 to about 70, from about 5 to about 55, or from about 10 to about 40 weight percent of functional fiber. For examples, see U.S. Patent Publication 20030211799.

A structural component may comprise a rolled paper rod wherein the matrix material paper is perforated at regular intervals to form attached "sheets" of paper, so that a sheet is substantially one layer of the multi-layer rolled rod. One can remove a layer from the surface of the rod by removing one sheet of the paper. As a layer is removed, the underlying sheet is exposed to the exterior and can provide a surface area for releasing an olfactory-active composition to the environment.

A matrix material may be an extruded plastic material which absorbs the olfactory-active composition. A matrix material may comprise a fibrous material comprised of a binder fiber adhered to a functional fiber, wherein the binder fiber is a staple bicomponent fiber oriented in substantially the same direction as the functional fiber. The functional fiber can be a staple or continuous fiber. Examples of suitable binder fibers include, but are not limited to, bicomponent fibers made of the following pairs of polymers: polypropylene/polyethylene terephthalate (PET); polyethylene/PET; polypropylene/Nylon-6; Nylon-6/PET; copolyester/PET; copolyester/Nylon-6; copolyester/Nylon-6,6; poly-4-methyl-1-pentene/PET; poly-4-methyl-1-pentene/Nylon-6; poly-4-methyl-1-pentene/Nylon-6,6; PET/polyethylene naphthalate (PEN); Nylon-6,6/poly-1,4-cyclohexanedimethyl-1 (PCT); polypropylene/polybutylene terephthalate (PBT); Nylon-6/co-polyamide; polylactic acid/polystyrene; polyurethane/acetal; and soluble copolyester/polyethylene. Examples of functional fibers include, but are not limited to, nylons, cellulose-based materials, polyvinyl alcohols (e.g., phosphorylated polyvinyl alcohol), superabsorbent fibers, carbon fibers, glass fibers, ceramic fibers, and acrylic fibers. Fibrous materials may have a density of from about 0.15 g/cm$^3$ to about 0.8 g/cm$^3$, from about 0.2 g/cm$^3$ to about 0.65 g/cm$^3$, and from about 0.25 g/cm$^3$ to about 0.5 g/cm$^3$.

The matrix material may be selected so as to provide controlled release of all or a portion of an olfactory-active composition, or to aid in control of the release of an olfactory-active composition. For example, a paper matrix may be provided that has a desired porosity. Higher porosity generally allows for faster release of an olfactory-active composition, and lower porosity generally allows for slower release. Additionally, the matrix material may comprise fibers having differing absorbance rates, which may affect the release rate of an olfactory-active composition. A matrix may be made from one or more differently absorbing or releasing fibers and such differing fibers may or may not provide for differing release rates of an olfactory-active composition. For example, a matrix made from 50% bamboo fiber and 50% paper fiber would release an olfactory-active composition at a rate different from that of a matrix made from 100% bamboo fibers or 100% paper pulp fibers. For example, the matrix may comprise a sponge or sponge-like element.

A matrix material may comprise a gel material. A gel matrix material may be of sufficient physical integrity as to hold its shape continuously. For example, a gel matrix material, comprising an olfactory-active composition, may be formed into a shape, such as a rod, and maintain the rod shape throughout its existence. Alternatively, a gel matrix material may be surrounded by another material that provides the structural shape to form the structural component of an article of the present invention. For example, a gel comprising an olfactory-active composition, such as a fragrance composition, may be surrounded by a plastic sheath that maintains the gel in a particular shape. A portion of the plastic sheath may be removed to allow for release of the olfactory-active composition from the gel and the article. A gel matrix material may be rolled to form a structure, for example, a rod-shaped structure, and the gel may comprise an olfactory-active composition. Gel matrix material compositions are known in the art and one of skill can combine a gel with an olfactory-active composition.

Optionally, aroma-releasing polymeric gel matrices may contain one or more additional materials that control evaporation and/or firmness of the polymeric gel matrix-Evaporation and/or Firmness Controlling Agent (EFCAs). Useful EFCAs include, but are not limited to, the following esters: acetates, adipates, azeleates, benzoates, caprylamides, capramides, caprates, citrates, cocoates, fumarates, glutarates, glycolates, heptanoates, isobutyrates, isophthalates, laurates, linoleates, maleates, mellitates, myristates (e.g., isopropyl myristate), octanoates, oleates, palmitates (e.g., isopropyl palmitate), pelargonates, phosphates, phthalates, ricinoleates, sebacates, stearates, succinates, toluates, toluamides, tallates, benzyl benzoate, di-2-ethylhexyl phthalate, proprietary blend of esters and phthalates, diethyl phthalate, dioctyl terephthalate, dioctyl adipate, hexanedioic acid polymer with 1,4-butanediol and 1,2-propanediol didecanoate, benzyl3-isobutyryloxy-1-isopropyl-2,2-dimethyl-propyl phthalate, and decanoates. Other suitable EFCAs include dipropylene glycol, hexylene glycol, isoparafinic hydrocarbons, including those sold under the tradename Isopar M by ExxonMobil (Houston, Tex.), polymeric PVC plasticizers, including those sold under the Tradename Admex by Velsicol Chemical Corp. (Rosemont, Ill.), and odorless mineral spirits.

A matrix material may comprise absorbent compositions. For example, a matrix material may comprise chalk, which is composed mostly of calcium carbonate with minor amounts of silt and clay, or the mineral gypsum (calcium sulfate). Such a chalk composition may be formed into a rod made of compressed powder, of any desired length. The structural component of chalk matrix material may be treated as described herein for other materials or structural components such as coated, colored and/or sheathed.

An aspect of the present invention comprises an article made with matrix materials that are stable, in that the matrix does not readily decompose, fall apart, unravel, shred, fracture, break or tear. Once formed, the matrix material is sufficiently sturdy to remain substantially intact when exposed to the environment or its intended use. An aspect of a matrix material is that the material is not brittle or friable to the touch and handling the matrix material in a typical use or manner does not cause breakage or pieces to dislodge. An aspect of the present invention comprises an article made with biodegradable matrix materials. An aspect of the present invention comprises an article made with recycled materials, or may be recyclable. Such materials may be fully or partially made with recycled material.

A treatment of the matrix material may occur or be applied before, or after, an olfactory-active composition is added to the matrix material. One or more treatments may be used with a particular matrix, and an olfactory-active composition may be added to the matrix before or after any one or all of the treatments to the matrix. One or more treatments may be controlled release elements of the article. One or more treatments may increase or decrease the rate of release of the fragrance from the article.

A coating applied to a matrix material or to a structural component may function as a barrier and thus retard release of an olfactory-active compound from the matrix material or structural component. As used herein, a coating, applying a coating and a coating composition refer to providing this barrier function to a matrix material or a structural component. Coating of a matrix material may occur before the matrix material is formed into the structural component of an article or may occur after the structural component is formed. For example, a paper may be coated with a wax while the paper is in a sheet or roll form, and the coating may be over all or a portion of the paper. The wax coating may be over an area of the paper, for example the wax coating covers an area an inch from one margin, or the coating may cover the paper from margin to margin but only be applied on the paper roll every other meter, so that some of the roll is coated and some is not. A coating applied to a matrix material may be in a pattern, such as a grid, applied to cover one entire surface, or may be randomly applied.

Coating compositions may comprises waxes, including but not limited to soy waxes, paraffins, and bees waxes. The wax may be coated onto a matrix material or a structural component using a flood coating method, wherein a wax is diluted in a solvent, such as a volatile solvent, and all outer surfaces are uniformly coated, for example, with a 1-10 micron layer of wax. A wax may be diluted in pentane. The coating may coat outer surfaces, including an outer surface that forms the inner surface that would be next to a core material. For example, in a rod shaped article shaped like a drinking straw, both the outer surface and the inner bore surface may be coated with a material, such as a wax. Waxes contemplated by the present invention comprise waxes known to those skilled in the art. A hydrophobic or hydrophilic solvent may be used in a coating composition.

Microcrystalline waxes differ from refined paraffin wax in that the crystal structure is more branched and the carbon chains are longer. These waxes are tougher, more flexible and have higher tensile strengths and melting points. They are also more adhesive, and they bind solvents, oil, etc., and thus prevent the sweating-out of compositions. Polyethylene waxes are manufactured from low molecular weight, high-density raw materials, designed to give the particular performance characteristics required by industry.

Waxes that may be used as coating compositions comprises waxes that soften or melt at a temperature about 150 F, or in excess of 200 F. For example, the High-Melt Straight Paraffin product from International Group Inc, IGI 1260-SLAB has a melting point of 163 F. Synthetic hydrocarbon waxes may have high melting points—e.g. 210 F.

Coating compositions may comprise acrylates. For example, coating compositions may be made with polyester polymers, such as polylactide, polyglycolide or polycaprolactone, or a polyester copolymer selected from poly(lactide/glycolide) acid (PLGA) or poly(lactid-co-.epsilon.-caprolact-one) (PLCL), alkyl- or alkoxyalkyl-2-cyanoacrylates such as n-butyl-2-cyanoacrylate or 2-methoxybutyl-2-cyanoacrylate, crosslinked cyanoacrylate, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene; and plasticizers such as dioctyl phthalate, dimethyl sebacate, trethyl phosphate, tri(2-ethylhexyl)phosphate, tri(p-cresyl)phosphate, glyceryl triacetate, glyceryl tributyrate, diethyl sebacate, dioctyl adipate, isopropyl myristate, butyl stearate, lauric acid, dibutyl phthalate, trioctyl trimellitate, and dioctyl glutarate.

Coating compositions may include polymers or copolymers containing, for example, caprolactone, poly-.beta.-hydroxybutyrate, delta-valerolactone, as well as polyvinylpyrrolidone, polyamides, gelatin, albumin, proteins, collagen, poly(orthoesters), poly(anhydrides), poly(.alpha.-cyanoacrylates), poly(dihydropyrans), poly(acetals), poly(phosphazenes), poly(urethanes), poly(dioxinones), cellulose, proteins and starches. A coating contemplated by the present invention comprises Krylon® Triple-Thick crystal clear glaze, commercially available from Krylon Products Group, Cleveland, Ohio.

The matrix material may also be coated after the matrix material is formed into the structural component of an article. For example, if a structural component is a rod, a coating may be applied to one or both of the ends of the rod. A coating may be applied to all or a portion of a structural component, such as on one side. A coating may be applied uniformly to a structural component or may be applied in a pattern or random application, such as spraying or sputtering.

The coating may function as a control release element of an article. A pattern coating may act as a screen door so as to impede some materials and allow others to pass. A pattern coating may be in a grid, in stripes, in any determined pattern or in no particular pattern, such as randomly applied. For example, adding a wax or plastic coating to a structural component may impede the release of an olfactory-active composition from an article. The coating may or may not degrade with time. For example, if the coating impedes the release of an olfactory-active composition, with time, as the coating degrades, there is more surface area for release of fragrance and less impedance of an olfactory-active composition release. Another example of coating provides for shielding or directing an olfactory-active composition in a particular direction. A structural component may be coated in a particular area and prevent release of an olfactory-active composition in that area. For example, if an article, comprising a fragrance olfactory-active composition, is placed with delicate foliage, the side of the article facing the foliage can be coated to prevent fragrance release toward the foliage and avoid any effects on the foliage.

A coating may function as a control release element for the release of an olfactory-active composition from an article of the present invention. A coating may allow an article to provide a particular level of an olfactory-active composition from the article for a determined time period. A coating may allow for a precise control release rate. For example, a coating on a matrix material may inhibit release of an olfactory-active composition so that an olfactory-active composition is released over a longer time period than is an uncoated matrix material.

Matrix material may undergo other treatments, which may be optional, such as dying of the matrix material. Dyes include natural and synthetic dyes, water-resistant dyes, oil-resistant dyes, and combinations of water- and oil-resistant dyes. Dyes may be selected based on the composition of the matrix material, and is well within the skill of those in the art. Suitable water-resistant dyes include oil soluble dyes and wax soluble dyes. Examples of oil soluble dyes include Pylakrome Dark Green and Pylakrome Red (Pylam Products Company, Tempe Ariz.). Suitable oil-resistant dyes include water soluble dyes. Examples of water soluble dyes include FD&C Blue No. 1 and Carmine (Sensient, St. Louis, Mo.). A Lake type dye may also be used. Examples of Lake dyes are Cartasol Blue KRL-NA LIQ and Cartasol Yellow KGL LIQ (Clariant Corporation, Charlotte, N.C.). Pigments may also be used in coloring the matrix materials and may be added during or after the manufacture of the matrix material. Such coloring or dying methods are known to those skilled in the art, and any suitable dyes, pigments or colorants are contemplated by the present invention.

Paper or other matrix materials may be treated or undergo secondary processing before use in an article of the present invention. For example, there are many secondary processes, examples include sizing, calendering, glazing, saturation, coating, folding, corrugating, perforating, slitting, and sheeting. Sizing is the process of lightly coating one or both surfaces of a paper with a starch solution to enhance surface properties. Calendering presses paper between two rolls under high pressure. As paper density and surface smoothness increase, porosity and thickness decrease. Glazing produces similar results, but uses a moving ball to apply high pressure to only one side of the paper. Saturation is an immersion process in which paper is fully wetted—typically with a latex dispersion—and subsequently dried. Coating applies one or more layers of material to one or both surfaces of a paper. For example, paper may be coated with wax. A coating may be applied as a liquid that then solidifies on a matrix material, or a coating may be a tape or sleeve that is applied to the matrix material or over all or a portion of the matrix material. For example, a matrix material may be dipped into a coating, sprayed with a coating, or a coating may be a tape that is wrapped around all or a portion of the matrix material. In another aspect, where the matrix material is formed into a rod, a sleeve of fluid impervious plastic is slipped over one end of the rod to cover the bottom and lower edge of the rod. A matrix material may be perforated in one or more sites. For example, a paper to be used in a rolled paper rod article may have multiple pinprick holes made in the paper prior to rolling. Such pinprick holes may form capillaries within the rolled rod and control movement and release of an olfactory-active composition. Such perforations may be added to the matrix material after formation into the structural component.

Matrix materials may be dyed for many reasons, such as so that an article will blend in with the environment it is used in, to mask the color of an olfactory-active composition, or so that the article may be noticed because of its appearance. A matrix material or a structural component may be dyed or colored with one or more colors or hues, or may have a dappled or patterned appearance. Colors or dyes may be applied to a matrix material or to a coating that is then applied to a matrix material. A water-resistant dye may be dissolved in a hydrophobic solvent. Suitable hydrophobic solvents include Isopar M, petroleum distillates, mineral oil, short or long chain alcohols, fragrances, fragrance raw materials, essential oils and other hydrophobic liquids that will solubilize the dye. An oil-resistant dye may be solubilized using a hydrophilic solvent. Suitable hydrophilic solvents include water, short chain alcohols, short chain carboxylic acids and glycols. A combination oil- and water-resistant dye can be solubilized in a solvent into which it will dissolve. Suitable materials include short chain alcohols. In a method of making an article of the present invention, methanol is used to dissolve and solubilize a Lake dye.

Methods of making articles of the present invention comprise applying or providing one or more olfactory active compositions or compounds to a matrix material or a structural component. For example, a method of making an scented article of the present invention comprises admixing in a container an olfactory-active composition and a structural component, such as a rod made by winding a continuous sheet of porous and/or absorbent paper around a central axis. The continuous sheet of paper is the matrix material. Alternatively, the matrix material may be scented prior to forming the structural component, the wound paper rod. Where a matrix material undergoes these steps of incorporating one or more olfactory-active compositions into the absorbent matrix material, to form a scented matrix material, the steps of forming a structural component from the matrix material follows so as to form a scented article of the present invention.

A method of making a scented article of the present invention comprises providing an olfactory-active composition that may be applied to the matrix material or structural component. For brevity, methods are described where the matrix material is contacted by the olfactory-active composition, though this is not to be limiting of the invention. An olfactory-active composition may be applied to the matrix material by dipping, spraying, sputtering, absorbing, adsorbing or immersing a matrix material with an olfactory-active composition, or other methods known for applying a liquid, solid, gaseous or gel composition to a solid support.

A method for making a scented article comprises combining an olfactory-active composition and a matrix material or structural component in a container and applying a pressure above atmospheric pressure on the composition and the matrix material or structural component. For example, a fragrance composition and a structural component such as rolled paper rod were combined in a container in a pressure treating apparatus (a sealed container) and pressure was applied in a range from about 1 psi to about 40 psi, from about 5 psi to about 30 psi, or from about 10 psi to about 20 psi, at about 5 psi, at about 10 psi, at about 15 psi, at about 20 psi, at about 25 psi, at about 30 psi, at about 35 psi, at about 40 psi, and pressures thereinbetween. The pressure may be applied for a period of time from about 10 minutes to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of olfactory-active compositions to a matrix material or structural component to achieve a desired load of the olfactory-active composition(s) to the matrix material or structural component or release of the olfactory-active composition from the matrix material or structural component.

A method for making a scented article comprises combining an olfactory-active composition and a matrix material or structural component in a container and applying a vacuum below atmospheric pressure on the composition and the matrix material or structural component. For example, a fragrance composition and a structural component such as rolled paper rod were combined in a container in vacuum apparatus and a vacuum was applied in a range from about 0.001 mm Hg to about 700 mm Hg, or from about 5 Kpa to about 35 kPa, from about 10 Kpa to about 25 kPa, from about 20 Kpa to about 30 kPa, from about 15 Kpa to about 25 kPa, from about 25 Kpa to about 30 kPa, at about 5 kPa, at about 6 kPa, at about 7 kPa, at about 8 kPa, at about 9 kPa, at about 10 kPa, at about 15 kPa, at about 16 kPa, at about 17 kPa, at about 18 kPa, at about 19 kPa, at about 20 kPa, at about 22 kPa, at about 24 kPa, at about 26 kPa, at about 28 kPa, at about 30 kPa, and vacuums thereinbetween. The vacuum may be applied for a period of time from about 10 minutes to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of olfactory-active compositions to a matrix material or structural component to achieve a desired load of the olfactory-active composition(s) to the matrix material or structural component or release of the olfactory-active composition from the matrix material or structural component.

A method of making a scented article of the present invention may comprise pressure and vacuum steps. An olfactory-active composition and a matrix material may be combined and undergo vacuum treatment and pressure treatment, in no particular order. For example, an olfactory-active composition and a matrix material were combined in a container in an air-tight apparatus and a vacuum of 20 mm Hg to 80 mm Hg was applied for about 1 minute to 10 hours. Pressure treatment of 1 psi to 40 psi may be applied for about 10 minutes to about 10 hours and the time and amount of vacuum or pressure treatment may vary and depend upon the amount of olfactory-active composition to be loaded in the matrix material or structural component, the type of matrix material used, the intended use of the article, and other characteristics of scented articles.

A method for making a scented article comprises adding an olfactory-active composition to a matrix material, comprising placing one or more matrix materials or one or more structural components in a closed container under a vacuum, such as about 0.1 to 700 mm Hg, maintaining the vacuum for 1 minute to 1 hour, for about 10 minutes, for about 15 minutes, for about 30 minutes, for about 45 minutes, introducing at least one olfactory-active composition in an amount sufficient to cover a portion of the one or more matrix materials or one or more structural components, optionally while maintaining the vacuum, then pressurizing the closed container containing the one or more matrix materials or one or more structural components and the at least one olfactory-active composition to 10-40 psi, or 500 to 2000 mmHg for a period of time. The period of time may be from 1 minute to 10 hours, for 15 minutes, for 30 minutes, for 1 hour, for 2 hours, for 3 hours, for 4 hours, for 5 hours, for 6 hours, for 7 hours, for 8 hours, for 9 hours, for 10 hours, or longer if desired for providing an adequate load of olfactory-active composition to a matrix material. Release of the pressure and removal of the matrix material or structural component comprising the absorbed olfactory-active composition follows.

A method for making a scented article, comprises, a) applying a vacuum in a closed container containing at least one structural component; b) adding a sufficient amount of a liquid olfactory-active composition to the closed container; c) maintaining the vacuum; d) releasing the vacuum and pressurizing the closed container so that a pressure is maintained for a time sufficient for a portion of the olfactory-active composition to be retained by the structural component. A method for making a scented article comprises a) applying a vacuum in a closed container containing at least one structural component; b) adding a sufficient amount of a liquid olfactory-active composition to the closed container to cover the desired portion of the at least one structural component; c) maintaining the vacuum for a desired time period; d) releasing the vacuum and removing the liquid; and optionally, e) applying a vacuum to the container comprising the at least one structural component.

Olfactory-active compounds useful in the present invention include but are not limited to, esters, terpenes, cyclic terpenes, phenolics which are also referred to as aromatics, amines and alcohols. For example, furaneol 1-hexanol, cis-3-Hexen-1-ol, menthol, acetaldehyde, hexanal, cis-3-hexenal, furfural, fructone, hexyl acetate, ethyl methylphenylglycidate, dihydrojasmone, wine lactone, oct-1-en-3-one, 2-Acetyl-1-pyrroline, 6-acetyl-2,3,4,5-tetrahydropyridine, gamma-decalactone, gamma-nonalactone, delta-octalactone, jasmine, massoia lactone, sotolon ethanethiol, grapefruit mercaptan, methanethiol, 2-methyl-2-propanethiol, methylphosphine, dimethylphosphine, methyl formate, nerolin tetrahydrothiophene, 2,4,6-trichloroanisole, substituted pyrazines, methyl acetate, methyl butyrate, methyl butanoate, ethyl acetate, ethyl butyrate, ethyl butanoate, isoamyl acetate, pentyl butyrate, pentyl butanoate, pentyl pentanoate, isoamyl acetate, octyl acetate, myrcene, geraniol, nerol, citral, lemonal, geranial, neral, citronellal, citronellol, linalool, nerolidol, limonene, camphor, terpineol, alpha-ionone, terpineol, thujone, benzaldehyde, eugenol, cinnamaldehyde, ethyl maltol, vanillin, anisole, anethole, estragole, thymoltrimethylamine, putrescine, diaminobutane, cadaverine, pyridine, indole and skatole. Most of these are organic compounds and are readily soluble in organic solvents, such as alcohols or oils. Fragrance includes pure fragrances such as those including essential oils and are known to those skilled in the art. Water-based odorous compounds and other odorus compositions are also contemplated by the present invention.

Fragrance oils as olfactory-active compounds or compositions usually comprise many different perfume raw materials. Each perfume raw material used differs from another by several important properties including individual character, and volatility. By bearing in mind these different properties, and others, the perfume raw material can be blended to develop a fragrance oil with an overall specific character profile. To date, characters are designed to alter and develop with time as the different perfume raw materials evaporate from the substrate and are detected by the user. For example perfume raw materials which have a high volatility and low substantivity are commonly used to give an initial burst of characters such as light, fresh, fruity, citrus, green or delicate floral to the fragrance oil which are detected soon after application. Such materials are commonly referred to in the field of fragrances as "top notes". By way of a contrast, the less volatile, and more substantive, perfume raw materials are typically used to give characters such as musk, sweet, balsamic, spicy, woody or heavy floral to the fragrance oil which, although may also be detected soon after application, also last far longer. These materials are commonly referred to as "middle notes" or "base notes". Highly skilled perfumers are usually employed to carefully blend perfume raw materials so that the resultant fragrance oils have the desired overall fragrance character profile. The desired overall character is dependent both upon the type of composition in which the fragrance oil will finally be used and also the consumer preference for a fragrance.

In addition to the volatility, another important characteristic of a perfume raw material is its olfactory detection level, otherwise known as the odor detection threshold (ODT). If a perfume raw material has a low odor detection threshold, only very low levels are required in the gas phase, or air, for it to be detected by the human, sometimes as low as a few parts per billion. Conversely, if a perfume raw material has a high ODT, larger amounts or higher concentrations in the air of that material are required before it can be smelt by the user. The impact of a material is its function of its gas phase or air concentration and its ODT. Thus, volatile materials, capable of delivering large gas-phase concentrations, which also have low ODTs, are considered to be impactful. To date, when developing a fragrance oil, it has been important to balance the fragrance with both low and high volatility raw materials since the use of too many high volatility materials could lead to a short lived, overwhelming scent. As such the levels of high odor impact perfume raw materials within a fragrance oil have traditionally been restricted.

As used herein the term "fragrance oil" relates to a perfume raw material, or mixture of perfume raw materials, that are used to impart an overall pleasant odor profile to a composition, preferably a cosmetic composition. As used herein the term "perfume raw material" relates to any chemical compound which is odorous when in an un-entrapped state, for example in the case of pro-perfumes, the perfume component is considered to be a perfume raw material, and the pro-chemistry anchor is considered to be the entrapment material. In addition "perfume raw materials" are defined by materials with a ClogP value preferably greater than about 0.1, more preferably greater than about 0.5, even more preferably greater than about 1.0. As used herein the term "ClogP" means the logarithm to base 10 of the octanol/water partition coefficient. This can be readily calculated from a program called "CLOGP" which is available from Daylight Chemical Information Systems Inc., Irvine Calif., USA. Octanol/water partition coefficients are described in more detail in U.S. Pat. No. 5,578,563.

Examples of residual "middle and base note" perfume raw materials include, but are not limited to, ethyl methyl phenyl glycidate, ethyl vanillin, heliotropin, indol, methyl anthranilate, vanillin, amyl salicylate, coumarin. Further examples of residual perfume raw materials include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral, intreleven aldehyde.

Examples of volatile "top note" perfume raw materials include, but are not limited to, anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, iso propyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, cis 1,3-oxathiane-2-methyl-4-propyl.

Other useful residual "middle and base note" perfume raw materials include, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Other volatile "top note" perfume raw materials include, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

In the past, many attempts have been made to delay the volatility profiles of fragrance oils within many types of compositions to extend the overall fragrance effect. For instance the fragrance oil may be formulated to include a higher proportion of perfume raw materials with a low volatility and which are therefore more substantive on the substrate. This may restrict the fragrance character that can be achieved over time. Another approach has been to chemically, and reversibly, modify the perfume raw materials to a pro-perfume compound which is disclosed in patent applications WO 98/47477; WO 99/43667; WO 98/07405; WO 98/47478; all of which are incorporated herein by reference. The resultant pro-perfumes are not themselves volatile but, after the chemical modification is reversed, usually by hydrolysis upon application to the substrate, the perfume raw material is released and can then evaporate in the usual way. In these examples the release rate of the perfume raw materials is controlled by the reaction rate of the pro-perfume to perfume raw material transformation.

Olfactory-active substances comprise compositions comprising compounds, mixtures or suspensions of odorous compounds that neutralize, cover or eliminate odors. For example, cyclodextrins are effective at providing odors and also at trapping odors, which may neutralize or eliminate an existing odor. Repellents may be one or more compounds that repel other organisms, such as insects. For example, compositions made from natural oils are found to be excellent insect repellents. See U.S. Patent Application Pub. No. 2007/0224232, which is incorporated in its entirety, for examples of effective insect repellent compositions.

A fragrance composition may be one compound or a mixture or suspension of one or more compounds, and the present invention comprises one or more of such fragrance compositions. An aspect of an article comprises other compositions, which may be used with fragrance compositions or in place of fragrance compositions and comprises compositions comprising odorous substances such as those used as air fresheners, sanitizers, or deodorizers, or compounds which remove odors, including but not limited to, cyclodextrins and compounds which bind to hydrophobic compounds that cause odors. An example of such a composition is sold as Febreeze® which include a modified starch compound An olfactory-active substance composition may comprise a material, such as a volatile material, including but not limited to fragrance, perfume, essential oil, solvent, deodorizer, malodor counteractant, insect repellant, and have scenting or perfumery activity alone or in combination with antimicrobial, insecticide, or pesticide activity. At least a portion of the olfactory-active substance composition is released when an article is exposed to ambient air. For example, a portion of an olfactory-active substance composition such as a fragrance is released when an article is exposed to ambient air.

An olfactory-active composition may be provided in an organic solvent, such as alcohol or an oil, may be provided in a mixture of organic and aqueous solvents, or may be provided in aqueous solvents such as water, saline or physiological salts. An olfactory-active composition may comprise an odorous compound or fragrance compound that may be modified, such as by chemical attachment of a substituent group, salt formation, crystal formation, or other chemical or physical change to the compound, to alter the activity of the compound, such as to alter its release rate from an article, maintenance of the compound in a volatile state, maintenance or release of the compound in the article, maintenance or release of the compound in the air, and maintenance or release of the compound in its solvent. Modified compounds may be used for detection of the presence of the olfactory-active composition in an environment, or for measuring the concentration of an olfactory-active composition or a component of the composition in the olfactory-active composition, in an article or in an environment.

An odorous compound may be provided in an olfactory-active composition. For example, an olfactory-active composition may comprise one or more fragrances. An olfactory-active composition may comprise a solvent. An olfactory-active composition may comprise one or more control elements, which are compounds or molecules that aid in odorous compound control, such as in release or maintenance of the odorous compounds in the solvent or article, maintenance of the odorous compounds in the air, or may aid in or retard the volatilization of the odorous compounds. An example of an olfactory-active composition odorous control element is a surfactant. Surfactants may be nonionic, anionic; cationic, or zwitterionic. One or more surfactants may be added to an olfactory-active composition and aid in the control of the release of the odorous compounds from the solvent solution, and ultimately, from the article. Control compounds may comprise compounds or molecules that degrade with time and once degraded, the odorous compound is more easily transmitted to the environment. Control elements may also be incorporated in the design of an article to aid in odorous compound control such as maintenance of the odorous compound release rate. Control elements may comprise compounds incorporated into the olfactory-active composition or that are associated with the structural components. For example, waxes or starches may aid in inhibiting or controlling the release of an olfactory-active compound. A starch or wax may be applied to the matrix material or the structural component, in any manner, such as covering one or more surfaces or in a particular pattern or a random pattern.

Odorous control elements may include compounds, molecules or solutions that affect the volatilization of the odorous compounds, mixtures or suspensions of the olfactory-active composition. A proportion of the olfactory-active composition may be such a control element solution. For example, olfactory-active composition may comprise 80-85% of a fragrance in an oil solvent with 15-20% of the composition comprising hexylene glycol.

Other compounds known in the art may be used as odorous control elements. For example, compounds comprising at least one β-carbonate or β-thio carbonyl moiety capable of liberating an active enone. As "active enone" it is intended, for example, an α,β-unsaturated ketone, aldehyde or carboxylic ester capable of bringing an odor benefit or effect into its surrounding environment, such as a perfuming ingredient, such as in a fragrance of the present invention. By "perfuming ingredient" it is meant a fragrance compound, which may be used in the perfumery industry, for example, a compound which is used as ingredient in perfuming preparations or compositions in order to impart a hedonic effect.

Compositions of the present invention comprise olfactory-active compositions provided in controlled release forms, including but not limited to, encapsulation, water-in-oil, oil-in-water emulsions, liposomes, or others. The present invention comprises encapsulation of the olfactory-active material in a protective coating. The protective coating may be a polymeric material. The polymeric material may protect the fragrance or olfactory material from evaporation, reaction, oxidation or otherwise dissipating with time.

Methods for encapsulation of fragrances may be taught in U.S. Pat. Nos. 2,800,457, 3,870,542, 3,516,941, 3,415,758, 3,041,288, 5,112,688, 6,329,057, and 6,261,483, all of which are incorporated by reference as if set forth in their entirety. Other methods of fragrance encapsulation may be found in the Kirk-Othmer Encyclopedia. Encapsulating polymers include those formed from melamine-formaldehyde or urea-formaldehyde condensates, as well as similar types of aminoplasts. Capsules made via the simple or complex coacervation of gelatin may be used. Capsules having shell walls comprised of polyurethane, polyamide, polyolefin, polysaccharide, protein, silicone, lipid, gelatins, modified cellulose, gums, polyacrylate, polyphosphate, polystyrene, and polyesters or combinations of these materials are also contemplated for the present invention.

U.S. Pat. No. 4,081,384 discloses a softener or anti-stat core coated by a polycondensate suitable for use in a fabric conditioner; U.S. Pat. No. 5,112,688 discloses selected fragrance materials having the proper volatility to be coated by coacervation with micro particles in a wall that can be activated for use in fabric conditioning; U.S. Pat. No. 5,145,842 discloses a solid core of a fatty alcohol, ester, or other solid plus a fragrance coated by an aminoplast shell; and U.S. Pat. No. 6,248,703 discloses various agents including fragrance in an aminoplast shell that is included in an extruded bar soap. The above U.S. patents are hereby incorporated by reference as if set forth in their entirety.

Encapsulation of fragrance in a polymeric shell may help prevent fragrance degradation and loss. Methods of aiding the deposition of encapsulated fragrances have been disclosed. U.S. Pat. No. 4,234,627 discloses a liquid fragrance coated with an aminoplast shell further coated by a water insoluble meltable cationic coating in order to improve the deposition of capsules from fabric conditioners. U.S. Pat. No. 6,194,375 discloses the use of hydrolyzed polyvinyl alcohol to aid deposition of fragrance-polymer particles from wash products. U.S. Pat. No. 6,329,057 discloses use of materials having free hydroxy groups or pendant cationic groups to aid in the deposition of fragranced solid particles from consumer products.

As used herein an "entrapment material" is any material which, after application of the composition to a substrate, suppresses the volatility of the perfume raw materials within the fragrance oil thus delaying their evaporation. It is not necessary that the entrapment material forms an association with the perfume raw material within the composition itself, only that this association exists on the substrate after application of the composition. Non limiting examples of mechanisms by which the delay in evaporation may occur are by the entrapment material reversibly or irreversibly, physically or chemically associating with the perfume raw material through complexing, encapsulating, occluding, absorbing, binding, or otherwise adsorbing the perfume raw materials of the fragrance oil.

As defined herein "reversible entrapment" means that any entrapment material: perfume raw material association in which the association can be broken down so that the entrapment material and perfume raw materials are released from each other. As defined herein "irreversible entrapment" means that the entrapment material: perfume raw material association cannot be broken down. As defined herein "chemically associated" means that the entrapment material and perfume raw material are linked through a covalent, ionic, hydrogen or other type of chemical bond. As defined herein "physically associated" means that the entrapment material and perfume raw material are linked through a bond with a weaker force such as a Van der Waals force. Highly preferred is that, upon the substrate, the entrapment material and the perfume raw material form a reversible physical or chemical association.

Entrapment materials for use herein are selected from polymers; capsules, microcapsules and nanocapsules; liposomes; pro-perfumes; film formers; absorbents; cyclic oligosaccharides and mixtures thereof. Preferred are pro-perfumes, absorbents and cyclic oligosaccharides and mixtures thereof. Encapsulating polymers include those formed from melamine-formaldehyde or urea-formaldehyde condensates, as well as similar types of aminoplasts. Additionally, capsules made via the simple or complex coacervation of gelatin are also preferred for use with the coating. Capsules having shell walls comprised of polyurethane, polyamide, polyolefin, polysaccharide, protein, silicone, lipid, gelatins, modified cellulose, gums, polyacrylate, polyphosphate, polystyrene, and polyesters or combinations of these materials are also functional.

On the substrate, where the perfume raw material and the entrapment material exist in an associated form, the weight ratio of high odor detection perfume raw material to entrapment material within the associated form may be in the range from about 1:20 to about 20:1, from about 1:10 to about 10:1, in the range from about 1:7 to about 7:1, in the range from about 1:5 to about 5:1, from about 1:3 to about 3:1 and in the range from about 1:2 to about 2:1.

Release of fragrance by article of the present invention may be controlled by one or more methods described herein. There are many methods described herein for controlling fragrance release and one or more of those methods may be used in any one article. The amount of fragrance contained by the article may control the period of time that fragrance is released into the environment in which the article is placed. Other methods or elements for controlling fragrance release or maintenance in an environment include, but are not limited to, the chemical compounds of the one or more fragrances used; modifications to one or more chemical compounds; other compounds in the fragrance composition including the fragrance solvent, surfactants, compounds known to affect the absorption or release rate of the fragrance compounds; the characteristics of the matrix material; how the matrix material is formed into a structural component; treatments to the matrix material such as coatings applied to the matrix; when in the treatment schema, if any, of the matrix material the fragrance composition is added to the matrix material; the formation of the structural component, and treatments to the structural component such as shaping it or application of coatings to all or a portion of the surface of the structural component.

An article of the present invention may change color in all or a portion of the structural component to indicate the amount of olfactory-active composition present in the structural component. For example, a composition comprising a color change indicator is incorporated into the structural component and after release of substantially all of the olfactory-active composition, the indicator changes color. Examples of a color change indicator includes but is not limited to, an organic dye, food grade dye, or mixtures thereof, FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, methyl violet, eosin yellow, malachite green, thymol blue, methyl yellow, bromophenol blue, congo red, methyl orange, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or mixtures thereof. The color change indicator may be responsive to pH.

An article of the present invention may be packaged for storage or delivery and sale. An article may be packaged to preserve an olfactory-active composition and to control release of an olfactory-active composition by preventing contact by ambient air. Many types of packaging material are capable of protecting article of the present invention. An aspect uses packaging materials through which an olfactory-active composition does not substantially diffuse or evaporate. Suitable materials for packaging an article include cellophane, polypropylene, some plastics, PET, polymers, fluorinated polyethylene, metalized films, metal, glass, glazed ceramics, and any other impervious material. A useful packaging material includes, but is not limited to, bi-oriented polypropylene, PET, or cellophane.

Article of the present invention may include an attachment element for attaching an article to another article or to other objects. Such an attachment element may comprise a hook, clip, or other means for attaching an article to a surface, another article, or another structure. For example, an article may have an attachment element that comprises a portion that attaches directly to the structural component and a portion that can be attached by a clip, hook, enclosed circle, hook and eye means (like Velcro®), string, prongs, loop, or adhesive to a surface, article or other structure such as a portion of a car, a fixture in a home or office, or a body. It is also useful for attachment elements to be shaped so that the structural component or article may be removed and replaced with a fresh structural component or article when the user so desires, whether or not the attachment element is removed from its attached site. Multiple structural components or article may be held in one attachment element. An article may be shaped to fit with an attachment element, such as by cutting, crimping, bending, shaping, etc. An attachment element may be used to hold or insert an article into an environment. For example, an attachment element may be a spike to which an article is attached and the combined attachment element/article is placed in a vase of flowers, or a bouquet, or into the dirt of a potted plant.

An article of the present invention may be placed in individual or multiple holders. A holder is a container in which an article may be placed. The use of such a holder may be beneficial to prevent contact between one or more article and other surfaces. Materials which are useful for a holder may not absorb an olfactory-active composition. Suitable materials for this include metal, ceramic, glass, plastic, and polymers. Materials that might not be otherwise suitable can be made suitable by coating at least a portion of the holder with a barrier that prevents contact between the holder and the article. The holder may be capable of holding one or more article. For holders capable of holding one or more article, one or more article with the same olfactory-active composition or with different olfactory-active composition may be placed into the holder at the same time.

A holder may comprise a container having at least one perforated surface. The perforated surface, meaning a surface having one or more apertures through which an olfactory-active composition can transit, may be made of any material, and for example, may be a wire mesh. One or more article are held by the holder and an olfactory-active composition is released from the one or more article. The olfactory-active composition may be released from the entire surface of the article, including the surface of the article located within the holder. An olfactory-active composition is transmitted through the one or more apertures of the holder and released to the environment.

For example, where an article is a rod-shaped structural component comprising an olfactory-active composition, one or more of the rod article are placed within a holder having at least one aperture. An olfactory-active composition is released from the rod throughout the length of the rod, and through the one or more apertures of the holder, so that an olfactory-active composition is not trapped within the holder. This is in contrast to a reed diffuser, which comprises wooden reeds standing in a container of scented oil. The fragrance can only be released from the upper portion of the reed as the oil is wicked up the reed. The container does not provide any fragrance release, and merely contains the liquid scented oil. Holders of the present invention may comprise decorative elements or attachment elements. Holders of the present invention may comprise other elements, such as heaters, fans, solar panels, be powered by electricity, or have moveable parts.

A holder may be used for one or more article that comprise a slidable or movable member for covering one or more apertures in a holder. For example, the holder may be a container having at least one side or surface that is perforated and has apertures through which an olfactory-active composition is transmitted. The holder may comprise another surface that moves or slides so as to cover the apertures and prevent an olfactory-active composition from transmitting through the holder. The slideable surface may be activated so that the apertures are not covered and an olfactory-active composition is transmitted. The slidable surface may remain in the open position or may be returned to the closed aperture position depending on the desired outcome. Such a slideable or moveable section or surface may provide an adjustable release rate control element for an olfactory-active composition.

The present invention comprises methods for using article for providing fragrance to an enclosed environment. Methods of the present invention comprise using an article to provide an olfactory-active composition to a contained space, such as a room, vehicle interior, an office, a dresser drawer, or a closet. Methods of the present environment comprise providing an olfactory-active composition to an area surrounding the article, which may or may not be an enclosed area. For example, an article may be worn as a personal body adornment and provide an olfactory-active composition to the person wearing it continuously, may be carried in a bouquet of flowers, or worn unseen to provide an odorous composition or odor neutralizing composition to the person.

In general, aspects of the present invention comprises articles, compositions and methods for making and using such articles and compositions. The present invention comprises a scented article, comprising, at least one olfactory-active composition, a structural component comprising an absorbent matrix material, and a coating composition covering a portion of the structural component, wherein at least one olfactory-active composition is releasably retained in the absorbent matrix material. The article comprising the absorbent matrix material is a pulp composition. The absorbent matrix material may be a sheet of porous paper wound about a central axis to form a multilayered paper rod. The wound paper may form a chamber through the central axis of the rod that is hollow and open at both ends. The chamber formed along the central axis of the rod may be filled with a gel or liquid. The absorbent matrix material has a void volume of about 1 mL to about 10 mL per structural component, depending on the matrix material. The article may have an absorbent matrix material that has a void volume of about 1.0% to about 99% of the total volume of the structural component. The gel or liquid comprises at least one olfactory-active composition. The coating covers more than 50% of the structural component. The coating covers substantially all of the structural component. The coating composition comprises a wax, soy wax, paraffin, bees wax, polyethylene wax, microcrystalline wax, waxes that soften or melt at a temperature greater than about 150 F, acrylates, polylactide, polyglycolide or polycaprolactone, or a polyester copolymer selected from poly(lactide/glycolide) acid (PLGA) or poly(lactid-co-.epsilon.-caprolactone) (PLCL), alkyl- or alkoxyalkyl-2-cyanoacrylates such as n-butyl-2-cyanoacrylate or 2-methoxybutyl-2-cyanoacrylate, crosslinked cyanoacrylate, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene; and plasticizers such as dioctyl phthalate, dimethyl sebacate, trethyl phosphate, tri(2-ethylhexyl)phosphate, tri(p-cresyl)phosphate, glyceryl triacetate, glyceryl tributyrate, diethyl sebacate, dioctyl adipate, isopropyl myristate, butyl stearate, lauric acid, dibutyl phthalate, trioctyl trimellitate, and dioctyl glutarate, Krylon® Triple-Thick crystal clear glaze.

The present invention comprises methods for making scented articles. A method for making a scented article comprises a) adding at least one liquid olfactory-active composition and at least one matrix material or at least one structural component, to a closed container; and in no particular order, b) applying a vacuum to the closed container and maintaining the vacuum for a period of time before releasing the vacuum; and c) pressurizing the closed container and maintaining the pressure for a period of time before releasing the pressure. Steps b) and c) may be repeated, may be repeated at least once. Applying a vacuum comprises a vacuum from about 0.001 mm Hg to about 700 mm Hg. Pressurizing the closed container comprises a pressure from about 10 to about 40 psi. The period of time for the vacuum or the pressure is from 1 minute to 10 hours. The olfactory-active composition comprises at least one of a fragrance, repellant, odor eliminating compound, aromatherapy compound, natural oil, water-based scent, odor neutralizing compound, or cyclodextrin. A sufficient amount of an olfactory-active composition comprises an amount that covers substantially all of the at least one structural component. The method may further comprise removing the at least one matrix material or at least one structural component from the closed container. The structural component comprises a sheet of absorbent paper wound about a central axis to form a multilayered paper rod. The portion of the olfactory-active composition that is absorbed by the structural component is from 2 to 200 mL.

A method for making a scented article may comprise a) adding at least one liquid olfactory-active composition and at least one matrix material or at least one structural component to a closed container; and optionally, b) applying a vacuum to the closed container and maintaining the vacuum for a period of time before releasing the vacuum; or c) pressurizing the closed container and maintaining a pressure for a period of time before releasing the pressure. Step b) or step c) is repeated, is repeated at least once. Both steps b) and c) may be repeated at least once. The method may comprise only applying a vacuum. The method may comprise only applying a pressure. The method may comprise applying both a vacuum and a pressure. Applying a vacuum comprises a particular vacuum from about 0.001 mm Hg to about 700 mm Hg or an increasing or decreasing range of a series of vacuum values from about 0.001 mm Hg to about 700 mm Hg. Pressurizing the closed container comprises a particular pressure from about 10 to about 40 psi, or an increasing or decreasing range of a series of pressure values from about 10 to about 40 psi. The period of time for the vacuum or the pressure is from 1 minute to 10 hours. The olfactory-active composition comprises at least one of a fragrance, repellant, odor eliminating compound, aromatherapy compound, natural oil, water-based scent, odor neutralizing compound, or cyclodextrin. A sufficient amount of an olfactory-active composition comprises an amount that covers substantially all of the at least one structural component. The method may further comprise removing the at least one matrix material or at least one structural component from the closed container. The structural component may comprise a sheet of absorbent paper wound about a central axis to form a multilayered paper rod. The portion of the olfactory-active composition that is absorbed by the structural component may be from 2 to 200 mL.

The methods of making an article may result in a scented article, comprising, at least one olfactory-active composition, a structural component comprising a matrix material of extruded or molded pulp composition, wherein the at least one olfactory-active composition is releasably retained in the absorbent material. The article may further comprise a coating covering a portion of the structural component. The pulp composition further comprises nanofibers. The pulp composition is extruded. The pulp composition is molded. The pulp composition further comprises additives.

It must be noted that, as used in this specification and the appended claims, the singular forms "a", "an", and "the" include plural referents unless the context clearly dictates otherwise. All patents, patent applications and references cited herein and included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

EXAMPLES

Example 1

An Exemplary Method of Making an Article

Loading Procedure for the Large-Tube Loading Apparatus Using Loading Results for nC12 and nC16.

The large tube loading apparatus has a main body that is a tube 18 inches long, with an internal diameter of 1.5 inches. It holds 30 0.23" rods up to 12 inches in length. It is equipped with threaded ends to allow capping with threaded plugs. The plugs have fittings, gauges and valves, used to provide the means to deliver and remove liquids as well as apply vacuum or pressure to the apparatus.

The top plug has a "cross" fitting that includes two ball valves and a gauge selected to register vacuum (to 30 inches of Hg) and pressure (to 100 psi). One ball valve has a barbed fitting to attach a vacuum pump, while the other ball valve has a Schrader valve stem to allow pressurization with a tire pump or compressor equipped with a tire fitting.

The bottom plug has a ball valve to allow introduction and removal of liquid to/from the device.

Thirty structural components made from paper from Plant D (referred to by letter D in examples), made as a continuous rolled paper rod, 9.5"-long, and approximately 0.2335" in diameter, were loaded with fragrance composition or a test organic solution mimicking a fragrance composition as follows:

Inserted structural components in the Large-Tube loading apparatus and sealed.

Pumped for 15 min at a vacuum <30 in Hg. Closed the valve connecting to the vacuum pump and observed vacuum gauge, for leaks.

If no significant leaks were observed, began introducing liquid (fragrance composition) by opening the bottom valve connected to the liquid reservoir. It took about 350 mL of liquid to completely cover the structural components. Once the liquid covered the structural components, stop the liquid flow. The vacuum should be between 25-30 in Hg.

Significant outgassing may be observed depending on the liquid boiling point. Some low-boiling point materials may "boil off" and contaminate the vacuum pump oil, thus, a cold vacuum trap was used to prevent damage to the pump.

Kept the liquid-filled container under vacuum for an additional 5 minutes to allow any entrapped gas remaining in the rods or liquid to escape.

Pressurized the liquid-filled loading apparatus to 40 psi for 15 minutes.

Released the pressure, and under atmospheric pressure, opened the bottom valve connected to the liquid reservoir. Allowed the liquid to drain into the liquid reservoir.

The liquid remaining in the loading apparatus can be drained by applying slight air pressure, e.g., 5-10 psi, and blowing the liquid into a suitable container After eliminating excess liquid, removed the structural components, now loaded with fragrance composition, from the loading container. They should be near-dry to the touch, and leave a faint liquid residue on an absorbent towel. Alternatively, a smaller apparatus was used.

Loading of a Small-Volume Apparatus Constructed from a 12"-Long, ½" Pipe. PVC Nipple, 2" Extension, Caps, and an Automobile Tire Valve Stem.

The tube holds 5 structural components made from paper from Plant D, made as a continuous rolled paper rod cut to 4.75" length, required approximately 25-30 mL of liquid. It was pumped down without liquid by removing the Schrader valve from the tire valve stem. Structural components were weighed after pumping down to ascertain the amount of moisture they held. After pump-down, the container was opened to the air, and then filled with liquid olfactory-active composition using a gas-tight syringe equipped with a Teflon tube (0.3 mm id). The Schrader valve was replaced in the stem; the container was capped, and pressurized to 30-40 psi.

Table 1 below shows results obtained with five half-rods loaded with nC12 using the small loader

TABLE 1

| rod # | L, in | weight | 10' vac | Δ weight | moisture | Load g | Total g | % load |
|---|---|---|---|---|---|---|---|---|
| I | 4.80 | 2.8580 | 2.8183 | 0.0397 | 1.4% | 3.8488 | 1.0305 | 37% |
| II | 4.78 | 2.8513 | 2.8425 | 0.0088 | 0.3% | 3.8560 | 1.0135 | 36% |
| III | 4.79 | 2.8492 | 2.8113 | 0.0379 | 1.3% | 3.9092 | 1.0979 | 39% |
| IV | 4.79 | 2.8707 | 2.8615 | 0.0092 | 0.3% | 3.8873 | 1.0258 | 36% |
| V | 4.78 | 2.8872 | 2.8562 | 0.0310 | 1.1% | 3.8885 | 1.0323 | 36% |
| pumped for ca30 min, in 12 in ½" pipe | | | | | | | | |
| pressurized to 20 psi after loading with 35 mL of C12 | | | | | | Average | | 36.7% |

The fourth column, labeled 10'vac, shows the weight of the rods after pumping down for ten minutes. The weight loss, attributed to moisture ranges from 0.3 to 1.4%. The large % error was attributable to the way the experiment was performed. The average load is 36.7%.

Results obtained using the Large-Tube loading apparatus are shown below in Table 2 for two loadings of nC12.

TABLE 2

| | # rods | total, g | loaded, g | gain, g | Load % |
|---|---|---|---|---|---|
| run#1 | 30 | 169 | 233 | 64 | 37.9% |
| run #2 | 30 | 169 | 232 | 63 | 37.3% |

Agreement was within experimental error of the balance used to acquire the data. The results were also in agreement with those obtained using the small loader (ave 37.6% vs. 36.7%).

Table 3 below shows results of loading 5 half-rods (4.75") with nC16. The table includes a second step of removing surface liquid.

TABLE 3

| rod # | L, in | Wt (g) | First blotting to dry surface | | | second blotting to dry surface | | |
|---|---|---|---|---|---|---|---|---|
| | | | loaded | total | % load | loaded | total | % load |
| A | 4.579 | 2.6604 | 3.7354 | 1.0750 | 40.4% | 3.7269 | 1.0665 | 40.1% |
| B | 4.603 | 2.7234 | 3.7884 | 1.0650 | 39.1% | 3.7823 | 1.0589 | 38.9% |
| C | 4.594 | 2.7641 | 3.7986 | 1.0345 | 37.4% | 3.7972 | 1.0331 | 37.4% |
| D | 4.592 | 2.7060 | 3.7984 | 1.0924 | 40.4% | 3.7913 | 1.0853 | 40.1% |
| E | 4.597 | 2.7354 | 3.8175 | 1.0821 | 39.6% | 3.8151 | 1.0797 | 39.5% |
| | | | | Average | 39.4% | | Average | 39.2% |

Interestingly, the C16 data showed an average loading of 39.3% as opposed to 36.7% for n-C12. The difference cannot be explained by density difference alone (C16=0.774 g/mL vs. C12=0.754 g/mL, at room temperature). The results obtained using the Large-Tube loading apparatus for nC12 and C16 are shown below along with the density and volume calculation.

TABLE 4

| | # | total, g | loaded, g | gain, g | load % | | |
|---|---|---|---|---|---|---|---|
| nC12 | | | | | | | |
| run#1 | 30 | 169 | 233 | 64 | 37.9% | | |
| run #2 | 30 | 169 | 232 | 63 | 37.3% | | |
| nC16 | 30 | 169 | 235 | 66 | 39.1% | | |
| Density of nC16 at room temperature. | | | 0.774 | | | VolC16 | 85.3 mL |
| Density of nC12 at room temperature. | | | 0.754 | | | VolC12 | 84.2 mL |

Note that the loadings with the small and Large-Tube loading apparatae showed the same trend; loadings of nC12 were smaller than those achieved with nC16. The difference was small, and was approximately 1 mL out of 85 mL or about 1.2%. The total volume, calculated for 30 structural components, 9.5"-long and 0.2335" diameter is 200.6 mL, thus, 85.3 mL represents a "void" or "accessible" volume of 42.5%.

Example 2

Observations and Loading Procedures for nC12, nC16 and Douglas Fir Perfume into 9.5" Rolled Paper Rods from Paper from Plant D Loading Procedure for Douglas Fir Perfume.

The loader, of Example 1 was modified by the installation of a tire stem and Schrader valve.

Thirty rolled paper rods 9.5"-long, 0.2335" dia, paper from Plant D, weighing 171.6 grams as received, were introduced to the large loader and loaded with Douglas Fir olfactory-active composition and the end sealed. Sealing of the apparatus is problematic, but is best done by wrapping the ends with a Teflon tape strip sufficiently long to wrap around the threaded-end six times. The loader is pressurized to about 40 psi and soap water used to test for leaks. If bubbles are detected, more Teflon tape needs to be used to fix the leak.

No leaks were detected, the loader was pumped down to a vacuum >30 in. Hg for 45 minutes. The pump is a two-stage, 3 cfm pump equipped with a trap kept at water-ice temperature. At 45 minutes, the vacuum pump was isolated by turning off the valve connecting the loader to the pump. The perfume was loaded in a clear graduated container connected to the bottom valve of the loader. The graduated container showed a volume of 450 mL. The bottom valve was opened carefully to introduce the perfume into the loader. Significant bubbling was observed. The bottom valve was turned off and the bubbling was allowed to subside. More liquid was introduced, by opening the bottom valve, until the rods tops were covered, and about one inch of liquid remained over the tops. At this point the vacuum was about 25 in. Hg. The loader was left under vacuum for 5 minutes. The liquid level dropped to about 0.5" above the rods tops. This level drop suggests liquid is being absorbed by the rods while the loader was under vacuum. More perfume was introduced and more bubbles were released. The final level was set at 3 inches above the rods tops, and the vacuum was measured at 20 in. Hg. At this point 385 mL of perfume composition was loaded into the loader.

The loader was pressurized to 44 psi and the liquid level dropped about 0.2". Initially, the pressure dropped with time, requiring re-pressurizing every about 2.3 minutes, having dropped 2-3 psi during that time. However, after 20 minutes the pressure stabilized, dropping about 1 psi in 15 minutes. The system was left under pressure for 3 hours.

After the pressurized period, the Schrader valve was used to relieve the pressure and drain most of the liquid by opening the bottom valve. The liquid was removed from the container prior to the next step. After closing the valve, the container was pressurized back to 40 psi. Excess liquid was drained by slightly opening the bottom valve. This process was repeated four times before removing the rods from the container.

Results.

The initial weight of 30 rods of paper from Plant D was 171.6 grams. After loading the rods weighed 244.5 g, or a loading by weight of 42.5%. The density of this perfume was measured at 0.879, thus, the free volume or available volume in the rods is calculated at 82.9 mL.

Loading Procedure for nC12 and nC16.

Thirty rods paper from Plant D 9.5"-long, and about 0.2335" in diameter, weighing 169 grams as received, were introduced to the loader and the end sealed. In these experiments weight was determined with a scale that only weighed to the nearest gram, as opposed to the scale used to measure loadings with the Douglas fir perfume.

The loader was pumped down for 15 min to a vacuum <30 inHg. No trap was used. The pump was isolated by closing the valve connecting the pump to the loader. The vacuum should hold for a few minutes if there are no significant leaks. No significant leaks were observed, and began introducing liquid by opening the bottom valve connected to the liquid reservoir. Once the liquid covered the rods, the bottom valve was closed to stop the liquid flow. The vacuum should still be between 25-30 in Hg. Kept the liquid-filled loader under vacuum for 5 additional minutes to allow any entrapped gas remaining in the rods or liquid to escape.

Pressurized the liquid-filled loader to 40 psi for 15 minutes. Released the pressure, and under atmospheric pressure, opened the bottom valve connected to the liquid reservoir. The liquid drained into the liquid reservoir.

The liquid remaining in the loader was drained by applying slight air pressure, e.g., 5-10 psi, and blowing the liquid into a suitable container.

After eliminating excess liquid, removed the rods form the loading container. They should be near-dry to the touch. Results.

The initial weight of 30 rods of paper from Plant D was 169 grams. The difference in this weight and the one reported for the Douglas Fir experiment above reflects the use of a different balance to obtain the hydrocarbon data. After loading the rods with nC12, the results of duplicate runs showed weights of 232 and 233 g. Thus, the load of nC12 averages 37.5% by weight, or a "free or available" volume of 84.2 mL assuming a density of 0.754 g/mL. After loading the rods with nC16, the rods weighed 235 g. Thus, the load is 39.1% by weight, or a "free or available" volume of 85.3 mL assuming a density of 0.774 g/mL.

Example 3

Summary of Release Data Obtained Using a Rapid-Testing Box and Rods Loaded with n-Hydrocarbons A Plexiglas box, was evaluated for applicability to the study of perfume release from rods of paper from Plant D. The Plexiglass box is about 1-foot tall, 1-foot wide, and about 6 inches deep. It has three fans on one side, each moving about 10 cfm, while the opposite side is left open but covered with a window screen to act as a diffuser, and to prevent particulate matter from entering the box. The box has a hinged front door and leveling screws.

The box has 8 small holes on the top, allowing the insertion of wire hooks used to suspend rods. The hooks were fixed in place with aluminum duct tape. The rods were fitted with a small cap and hung in the box. The rod numbers reflect the position within the box, i.e., 1 is farthest from the fans, and so on.

Two sets of rods were used. One set has a load of 37.5% w/w of n-C12, while the other has a 39.1% w/w load of C16. The difference in loading, by weight, likely reflects the density difference between those two materials. The loading procedure used was described in Examples 1 and 2. Two 9.5" rods were removed from each set and cut in half. The resulting two sets of four 4.7 in-long rods were fitted with caps and labeled 1-4 for nC16 and 5-8 for nC12. The half-rods hold a load of about 1.15 g of hydrocarbon each. They were hung inside the box in the order 1, 5, 2, 6, 3, 7, 4 and 8, alternating from C16 to C12, to determine if there were any positional effects. Weight losses as a function of time inside the box were recorded using a 4-place analytical balance, with a repeatability of ±0.1 mg. The dimensions of the analytical balance determined the choice to use 4.7" rods.

Results.
Rods Loaded with n-C12.

Figure 3:
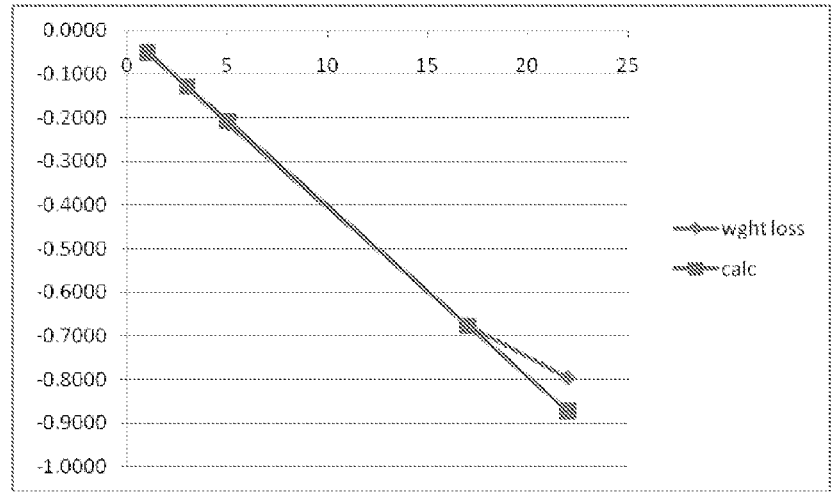
FIG. 3 is a graph of release of nC12 from a structural component, where the y axis is wt loss in grams and the x axis is time in hours.

Loss data for the first 22 hours inside the box, for nC12-loaded 4.7" rods, is shown below in tabular and graphical form, Table 5 and FIG. 3 weights in grams and time in hours. Thus, after only 22 hours, about 70% of the estimated load has been released to the air (0.80/1.15).

TABLE 5

| | Time, Hrs. | | | | |
|---|---|---|---|---|---|
| | 1 | 3 | 5 | 17 | 22 |
| C12-5 | −0.0431 | −0.1258 | −0.2037 | −0.6387 | −0.7855 |
| C12-6 | −0.0430 | −0.1279 | −0.2090 | −0.6817 | −0.7961 |
| C12-7 | −0.0409 | −0.1122 | −0.1814 | −0.5878 | −0.7458 |
| C12-8 | −0.0533 | −0.1563 | −0.2556 | −0.7918 | −0.8556 |
| Average weight | −0.0451 | −0.1306 | −0.2124 | −0.6750 | −0.7958 |
| stdev | 0.0056 | 0.0185 | 0.0312 | 0.0868 | 0.0454 |
| rel stdv | −12% | −14% | −15% | −13% | −6% |

| nC12, linearity 17 hours | | |
|---|---|---|
| time, h | wght loss | calc |
| 1 | −0.0451 | −0.05059 |
| 3 | −0.1306 | −0.12883 |
| 5 | −0.2124 | −0.20708 |
| 17 | −0.6750 | −0.67655 |
| 22 | −0.7958 | −0.87217 |

| 4 data points Regression Statistics | | |
|---|---|---|
| Multiple R | | 0.999864 |
| R Square | | 0.999729 |
| | Coefficients | StdError |
| Intercept | −0.01146 | 0.0040998 |
| X, g/H | −0.03912 | 0.0004555 |

The linearity of the nC12 release over the first 17 hours strongly suggests the nC12 is being released from the rod as if it was an immobilized liquid. The slope shown (X variable in the regression table above) is 39.1 mg/hour/rod.

The last data point, 22 hours, shows deviation from linearity. Though not wishing to be bound by any particular theory, it is theorized that at this point, a different release mechanism took place.

Example 4

Summary of Release Data Using Coated and Un-Coated Rods of Paper from Plant D Loaded with n-C12

The Plexiglas box, of Example 3 was used to study the release profile of coated and un-coated rods of paper from Plant D) loaded with n-C12.
Several coatings sufficiently thick (or efficient) to reduce the release rate of rods were tested.

Figure 4:
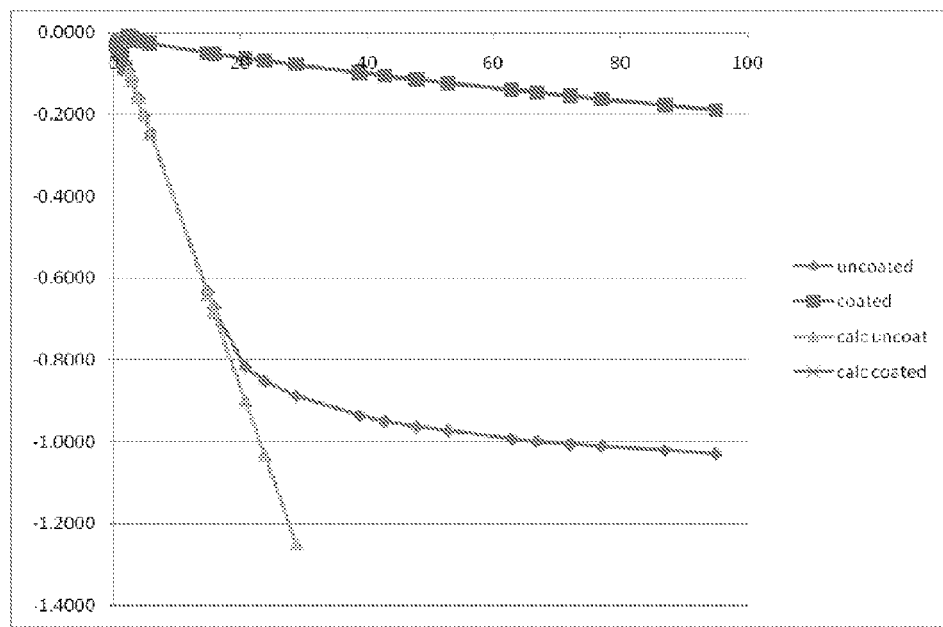
FIG. 4 is a graph of release from coated and non-coated structural components, where the y axis is wt loss in grams and the x axis is time in hours.

In one example, the rods were coated with Krylon® Triple-Thick crystal clear glaze. The results of this experiment are shown in FIG. 4 as weight loss, in grams, vs. hours.

The un-coated rods behaved as previously reported: linear loses with time, a slope of 0.0435 grams/hour for the first 17 hours, followed by an exponential release, approaching asymptotically the material load in the rod, about 1.15 g. The Krylon-coated rods showed a different release rate, ranging from 0.0020 grams/hour, for the 15-48 hour period, to 0.0016 grams/hour for the 48-95 hour period. Thus, there is a about 20× drop in the amount of material released from the rods.

The experiment shows the rate of release of loaded paper-based rods used to deliver organic compounds to the air can be reduced by coating the rods. The data also showed that the coating preserves the desirable linear delivery of the rods over most of their useful life.

Example 5

Summary of Release Data Using Coated and Un-Coated Rods of Paper from Plant D Loaded with Douglas Fir Perfume The Plexiglas box of Example 3 was used to study the release profile of coated and un-coated rods of paper from Plant D loaded with Douglas Fir perfume.

Nine and a half inches-long rods of paper from Plant D, loaded with Douglas Fir perfume as described in Examples 1 and 2, were cut in half. Each 4.7" half contains about 1.2 grams of perfume. Rods labeled 1-3 were left un-coated, while 4-6 were coated with Krylon, and dried in the Plexiglas box for 10 min. The rods were placed inside the box in the order 1, 4, 2, 5, 3, 6, with 1 placed farthest from the fans.

The coated rods had coating weights of 0.0440, 0.0498 and 0.0298 grams for rods 4, 5, and 6, respectively. Assuming a uniform coating, and a density of 1 gram/mL, the film thickness would range from 22 to 13μ. Because spraying from a can, by hand, was very unlikely to produce a uniform coating on round rods, the range was only an estimate of the actual film thickness on the rods.

Figure 5:
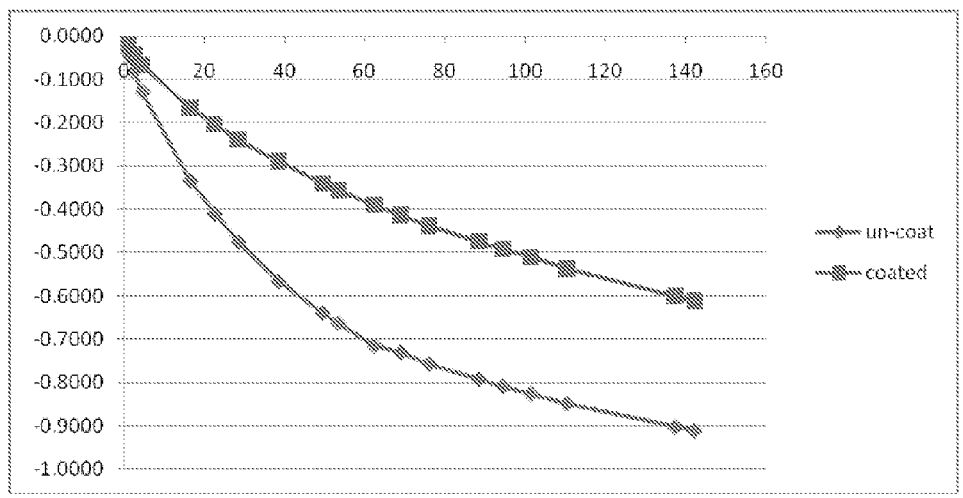
FIG. 5 is a graph of release from coated and non-coated structural components, where the y axis is wt loss in grams and the x axis is time in hours.

Results, shown in FIG. 5, represent the average weight loss of three half-rods (in grams) on y axis with time (hours) on the x axis.

The initial release of perfume, measured at 16-28 hours, was 0.0119 and 0.0061 grams per hour for un-coated and coated 4.7" rods, respectively. Thus, coating rods with Krylon produced a decrease in the release rate of the perfume loaded into the rods. The initial release rate is 2× smaller for the coated rods, thus, extending the lifetime of the rod.

The release rates measured after 110 hours were 0.0019 and 0.0024 grams per hour for un-coated and coated rods, respectively. The rate for the coated rods is greater than that for the un-coated rods, reflecting the extended "lifetime" of the rod.

Example 6

Summary Data of Rods of Paper from Plant D, Rods of Paper from Plant F and and Rods of Paper from Plant G Loaded with nC16 and Douglas Fir Perfume

Loading Data: Effect of Loading Techniques on Rods of Paper from Plant D

Loadings of rods of paper from Plant D, obtained using the large volume loader or a small-volume loader of Examples 1 and 2, and a variety of time- and vacuum/pressure-conditions, are shown in the Tables below.

TABLE 6

RODS OF PAPER FROM PLANT D
C12, Small-volume loader

| | |
|---|---|
| 1.040 | average grams per 4.7" rod |
| 1.379 | C12 volume (mL) |
| 3.343 | mL in 4.7" rod volume |
| 41.3% | occupied of "available volume" |
| 36.7% | C12 load by weight |

TABLE 7

C12, Large-volume loader

| | |
|---|---|
| 1.067 | average grams per 4.7" rod |
| 1.415 | C12 volume (mL) |
| 3.343 | mL in 4.7" rod volume |
| 42.3% | occupied of "available volume" |
| 37.9% | C12 load by weight |

TABLE 8

C12, Large-volume loader

| | |
|---|---|
| 1.050 | grams per 4.7" rod |
| 1.393 | C12 volume (mL) |
| 3.343 | mL in 4.7" rod volume |
| 41.7% | occupied of "available volume" |
| 37.3% | C12 load by weight |

The data shown in Tables 6-8 suggested that the properties of the two loaders and the different conditions employed to perform those experiments did not change the loading achievable with nC12. The data showed that the volume of the rods of paper from Plant D occupied by liquid is 42±1%. This percentage was constant over a wide range of experimental conditions.

Loading data: effect of loading nC16 and Douglas Fir into rods made with different papers. Data obtained with large-volume loader Loading data of rods of paper from Plant D with nC16 is shown below.

TABLE 9

C16 in rods of paper from Plant D

| | |
|---|---|
| 1.100 | grams per 4.7" rodrod |
| 1.421 | C16 volume (mL) |
| 3.343 | mL in 4.7" rod volume |
| 42.5% | occupied of "available volume" |
| 39.1% | C16 load by weight |

The nC16 percent load by weight was larger than that measured with nC12 (39.1 vs 37±1%, respectively) because of the higher density of nC16 (0.774 vs 0.754 g/mL). The available volume in the rod should be a constant determined by the matrix material structure. Once the weight loading was corrected for density, the percent occupied by volume remains constant (42±1%), as expected.

Loading data of rods of paper from Plant D loaded with Douglas Fir perfume is shown in Table 10.

TABLE 10

Douglas Fir in rods of paper from Plant D

| | |
|---|---|
| 1.215 | grams per 4.7" rod |
| 1.381 | D-F volume (mL) |
| 3.343 | mL in 4.7" rod volume |
| 41.3% | occupied of "available volume" |
| 42.5% | D-F load by weight |

The Douglas Fir load by weight is larger than that measured with nC16 and nC12 because it has a density of 0.88 g/mL. But, the available volume in the rod is 41.3%, within the expected experimental error.

Loading data of rods of paper from Plant F rods loaded with Douglas Fir (D-F) perfume is shown below

TABLE 11

| Douglas Fir in rods of paper from Plant F, Type 1 | |
|---|---|
| 1.45 | grams per half rod |
| 1.649 | D-F volume (mL) |
| 3.343 | mL in 4.7" rod volume |
| 49.3% | occupied of "available volume" |
| 57.8% | D-F load by weight |

The rods of paper from Plant F rods have a larger available volume than the rods of paper from Plant D (49 vs 42%, respectively). As a consequence, their load by weight is significantly greater.
Loading data of rods of one type of paper from Plant G loaded with Douglas Fir perfume is shown below in Table 12.

TABLE 12

| Douglas Fir in rods of paper from Plant G, Type 1 | |
|---|---|
| 1.39 | grams per half rod |
| 1.580 | D-F volume (mL) |
| 3.343 | mL in 4.7" rod volume |
| 47.3% | occupied of "available volume" |
| 50.4% | D-F load by weight |

Loading data of rods of paper of Type 2 from Plant G loaded with Douglas Fir perfume is shown below.

TABLE 13

| Douglas Fir in rods of paper from Plant G Type 2 | |
|---|---|
| 1.46 | grams per half rod |
| 1.660 | D-F volume (mL) |
| 3.343 | mL in 4.7" rod volume |
| 49.7% | occupied of "available volume" |
| 57.9% | D-F load by weight |

The rods of Type 2 paper from Plant G showed a larger available volume than the Type 1 rods of paper from Plant G, and load comparably to the rods of paper from Plant F.
Perforated Paper Matrix Material
To increase available volume a trial was made using perforated paper. Rods were made with paper from Plant D perforated by punching 1 mm-diameter holes separated by a distance of 1 mm. The results are shown in Table 14.

TABLE 14

| C16 in rods of paper from Plant D perforated with 1 mm dia holes. | |
|---|---|
| 1.153 | grams per 4.7" rod |
| 1.490 | C16 volume (mL) |
| 3.343 | mL in 4.7" rod volume |
| 44.6% | occupied of "available volume" |
| 51.0% | C16 load by weight |

Perforations achieved an increase in available volume for rods of paper from Plant D (44.6% vs 42±1%).

Example 7

Paper Rods Loaded by Soaking for Three Days

A Comparison of Loads and Release Rates with Rods Loaded by Means of a Vacuum/Pressure Procedure The ability to load rods by soaking in liquids for three days was evaluated with nC12 and Douglas Fir (D-F) perfume. Two rods types, rods of paper from Plant D and rods of Type 2 paper from Plant G, were used.
Loading Results.
Results and a comparison with previous loadings performed by a Vacuum/Pressure (Vac-Press) procedure previously described in Examples 1 and 2, are shown in Table 17.

TABLE 15

| | C12 Soaking rods of Type 2 paper from Plant G | | C12 Soaking rods of paper from Plant D | | D-F Soaking rods of paper from Plant D | |
|---|---|---|---|---|---|---|
| rods weight, unloaded | 40.98 | g | 45.04 | g | 45.08 | g |
| rods weight, loaded | 60.5 | g | 60.5 | g | 61.8 | g |
| % loaded by Weight | 48% | | 34% | | 37% | |
| load in 4.7" rod | 1.22 | g | 0.97 | g | 1.05 | g |
| | C12 Vac-Press rods of Type 2 paper from Plant G | | C12 Vac-Press rods of paper from Plant G | | D-F Vac-Press rods of paper from Plant G | |
| % loaded by Weight | 55-58% | | 37-38% | | 42-43% | |

The results show that compared to the method of Examples 1 and 2, loadings attainable by soaking for three days are lower, e.g., rods of Type 2 paper from Plant G load 55-58% vs 48% of C12 by weight for the Vacuum/Pressure and soaking procedure, respectively. Release reproducibility. Though not wishing to be bound by any particular theory, it is currently thought that rods loaded by soaking were not uniformly loaded and therefore showed large standard deviations in delivery rates. This was shown in Table 18 as weight loss over time (hours), for three rods of paper from Plant D (D1-3) loaded by soaking with C12.

TABLE 16

| | hours | | | | |
|---|---|---|---|---|---|
| | 0.5 | 1 | 1.5 | 2 | 2.5 |
| D1 | −0.0245 | −0.0456 | −0.0666 | −0.0876 | −0.1088 |
| D2 | −0.0209 | −0.0393 | −0.0584 | −0.0762 | −0.0937 |
| D3 | −0.0165 | −0.0300 | −0.0433 | −0.0568 | −0.0708 |
| Average | −0.0206 | −0.0383 | −0.0561 | −0.0735 | −0.0911 |
| stdev | 0.0040 | 0.0078 | 0.0118 | 0.0156 | 0.0191 |
| rel stdv | −19% | −20% | −21% | −21% | −21% |

Note that the difference in mass released by rods D3 and D1 is initially as large as 50%, while the relative standard deviation is about 20%.
The release reproducibility obtained by loading rods with the procedure of Examples 1 and 2 is illustrated in Table 17, showing weight loss over time for rods of paper from Plant D loaded with C12.

TABLE 17

| | hours | | | | |
|---|---|---|---|---|---|
| | 0.75 | 1.75 | 2.25 | 2.75 | 3.75 |
| D1 | −0.0400 | −0.0932 | −0.1004 | −0.1254 | −0.1775 |
| D2 | −0.0334 | −0.0766 | −0.0876 | −0.1079 | −0.1491 |
| D3 | −0.0381 | −0.0810 | −0.0924 | −0.1122 | −0.1537 |

TABLE 17-continued

| | hours | | | | |
|---|---|---|---|---|---|
| | 0.75 | 1.75 | 2.25 | 2.75 | 3.75 |
| Average | −0.0372 | −0.0836 | −0.09347 | −0.11517 | −0.1601 |
| stdev | 0.0034 | 0.0086 | 0.0065 | 0.0091 | 0.0152 |
| rel stdv | 9% | 10% | 7% | 8% | 10% |

The data shows a much tighter release, with differences between rods typically less than 20%, and relative standard deviations typically 10% or less. We have observed this performance over a large number of studies.

Delivery Rates.

The rate of delivery data for rods of paper from Plant D loaded with C12 by soaking is shown below for two time intervals, 1-2.5 and 6.5-7.5 hours.

TABLE 18

SUMMARY OUTPUT

DOMTAR C12, 1-2.5 hours
Regression Statistics

| Multiple R | 0.999992 |
|---|---|
| R Square | 0.999983 |

| | Coefficients | Standard Error |
|---|---|---|
| Intercept | −0.00322 | 0.000188 |
| Loss, g/h | −0.03517 | 0.000102 |

DOMTAR C12, 6.5-7.5 hours
Regression Statistics

| Multiple R | 0.999936 |
|---|---|
| R Square | 0.999873 |

| | Coefficients | Standard Error |
|---|---|---|
| Intercept | 0.000322 | 0.003104 |
| Loss, g/h | −0.03923 | 0.000443 |

While probably not significant, the difference in rates between the two time periods, −0.0352 and −0.0392 g/hour, may have been caused by the time required to establish a steady-state equilibrium. Initially, towel-drying would disrupt the equilibrium at the rod surface, thus, the steady state could have been reached after the first few hours. Those rates are comparable to the −0.0391 g/hour reported for the Vacuum/Pressure loaded rods. This likely means that, as long as the same matrix material is used, the rates are determined only by the amount of free liquid in the rods. For rods of paper from Plant D, the free liquid is close to the 70% of the load, as previously reported.

More interesting is the difference between the rods of paper from Plant D and rods of Type 2 paper from Plant G Data for rods of Type 2 paper from Plant G loaded by soaking in C12 are shown below in Table 19.

TABLE 19

| SUMMARY OUTPUT Rods of Type 2 paper from Plant G C12, 1-2.5 hours | | SUMMARY OUTPUT Rods of Type 2 paper from Plant G C12, 6.5-7.5 | |
|---|---|---|---|
| Regression Statistics | | Regression Statistics | |
| Multiple R | 0.999954 | Multiple R | 0.999905 |
| R Square | 0.999907 | R Square | 0.999811 |

TABLE 19-continued

| SUMMARY OUTPUT Rods of Type 2 paper from Plant G C12, 1-2.5 hours | | | SUMMARY OUTPUT Rods of Type 2 paper from Plant G C12, 6.5-7.5 | | |
|---|---|---|---|---|---|
| | Coefficients | Standard Error | | Coefficients | Standard Error |
| Intercept | −0.0002 | 0.0003 | Intercept | 0.004711 | 0.002564 |
| Loss, g/h | −0.02404 | 0.000164 | Loss, g/h | −0.02657 | 0.000366 |

Figure 6:
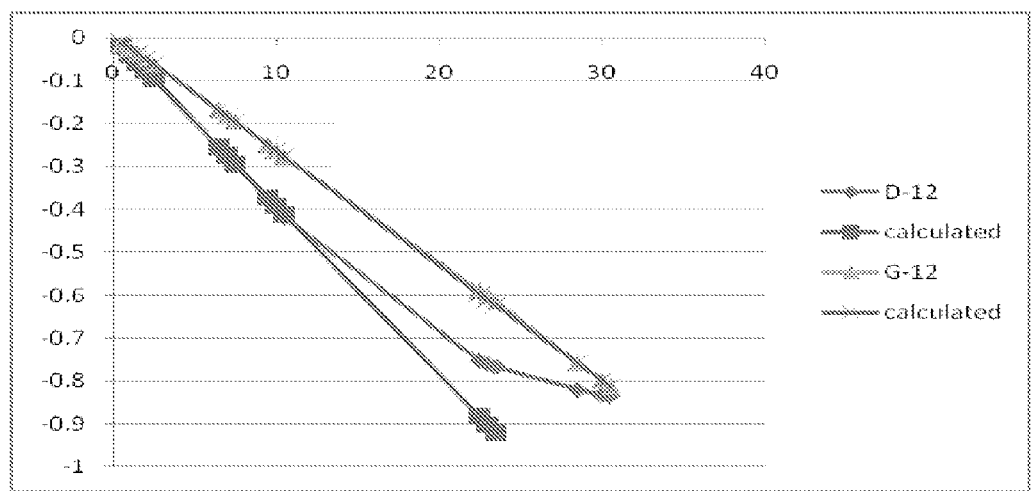
FIG. 6A is a graphs of release from structural components with differing matrix materials.
FIG. 6B is a graph of release from a structural component, where the y axis is wt loss in grams and the x axis is time in hours.

The relative standard deviations of rods of paper from Plant D and rods of Type 2 paper from Plant G loaded by soaking are comparable (about 20%). Although we would expect a relatively large error in the delivery rates as a consequence of the large standard deviations, the absolute rates between the two time periods are in close agreement, −0.0240 and −0.0266 g/hour. In spite of a much larger load (48% vs. 34% for rods of paper from Plant D), the rods of Type 2 paper from Plant G rates are smaller than the −0.039 g/hour reported for rods of paper from Plant D. The lower rates attainable with the rods of Type 2 paper from Plant G may be due to the paper's microstructure, and may achieve longer delivery times. See FIG. 6A.

The delivery of rods of paper from Plant D is linear for the first 15 hours, but deviates from linearity (shown by the squares) around the expected point. i.e., 70%. Thus, the line (small diamond) representing the delivery rate of rods of paper from Plant D begins to flatten out after about 15 hours: the slope changes from about 39 mg per hour for the first ten hours to 7 mg per hour at 30 hours.

By contrast, the rods of Type 2 paper from Plant Gate still delivering a constant rate at 30 hours: the slope a constant 26±1 mg over the 30 hour period shown below. Thus, while initially delivering a smaller amount of material per unit time to the environment, i.e., 26 vs. 39 mg/hour, the rods of Type 2 paper from Plant G deliver that amount linearly over a time span twice as long as possible with the rods of paper from Plant D. See FIG. 6B.

Figure 6B:
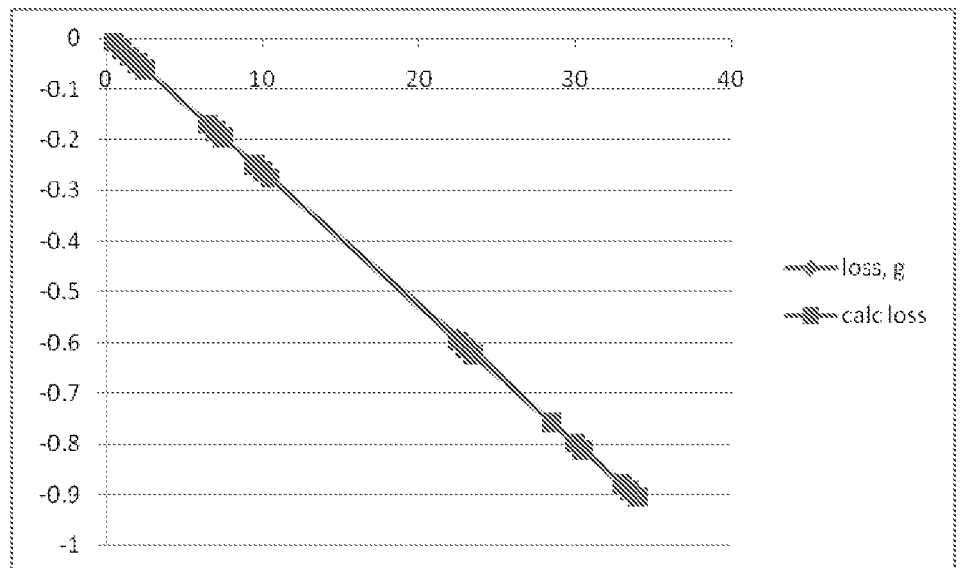

The FIG. 6B shows weight loss vs. hours in the rapid release box for rods of Type 2 paper from Plant G loaded with C12 by soaking. Over 70% of the mass loaded (0.9 g/1.22 g) is released to the air at a constant rate of 26 mg (0.026 g) per hour.

Example 8

Release Rates Using Krylon Clear Glaze 0500

Coatings were used to modulate delivery rates. Using rods of paper from Plant D loaded with Douglas Fir and coating them with Krylon 0500, purchased commercially and available from Krylon Products Group, Cleveland Ohio. This coating is film-like, soft, and with no surface discontinuities apparent under microscopic inspection.

Procedure.

Coating was done by fitting rods with caps, and suspending them on a horizontal rod. The rods were weighed prior to, and after spraying. A five minute drying time in the Plexi-glass rapid-test box of Example 3 was used before weighing. Five 9.5" rods of paper from Plant D loaded with Douglas Fir, and three 5.5" rods of paper from Plant G loaded with nC12, were sprayed with Krylon 0500 by moving the can across the rods at a distance of about 10 inches. The rods were rotated 180 degrees and the spraying repeated.

Result.

The coating of rods was done step-wise, and a decision to re-coat was made after measuring release rates. The initial results of coating 5.5" rods of paper from Plant G loaded with C12 are shown below in Table 21. To calculate rates, the average weight loss of three rods was used.

TABLE 20

|  | initial wgt 9:00 AM | 1 coat 9:30 AM | 0 9:40 AM | 1 9:50 AM | 2 10:50 AM | 2.5 11:20 AM |
|---|---|---|---|---|---|---|
| K-G12-1 | 4.9395 | 4.9788 | 4.9782 | 4.9669 | 4.9225 | 4.9011 |
| K-G12-2 | 4.9460 | 4.9828 | 4.9823 | 4.9728 | 4.9327 | 4.9135 |
| K-G12-3 | 4.9271 | 4.9702 | 4.9692 | 4.9614 | 4.9318 | 4.9173 |
| u-G12-4 | 4.8917 | 4.8917 | 4.8917 | 4.8847 | 4.8534 | 4.8370 |
| u-G12-5 | 4.9812 | 4.9812 | 4.9812 | 4.973 | 4.9334 | 4.9132 |
| u-G12-6 | 4.9035 | 4.9035 | 4.9035 | 4.8963 | 4.8637 | 4.8464 |

|  |  |  | 0 | 1 | 2 | 2.5 |
|---|---|---|---|---|---|---|
| K-G12-1 |  | 0.0393 |  | −0.0113 | −0.0557 | −0.0771 |
| K-G12-2 |  | 0.0368 |  | −0.0095 | −0.0496 | −0.0688 |
| K-G12-3 |  | 0.0431 |  | −0.0078 | −0.0374 | −0.0519 |
| u-G12-4 |  | 0 |  | −0.0070 | −0.0383 | −0.0547 |
| u-G12-5 |  | 0 |  | −0.0082 | −0.0478 | −0.0680 |
| u-G12-6 |  | 0 |  | −0.0072 | −0.0398 | −0.0571 |
| ave K-G12 |  |  |  | −0.0095 | −0.0476 | −0.0659 |
| stdv |  |  |  | 0.0018 | 0.0093 | 0.0128 |
| rel stdv |  |  |  | −18% | −20% | −19% |
| ave u-G12 |  |  |  | −0.0075 | −0.0420 | −0.0599 |
| stdv |  |  |  | 0.0006 | 0.0051 | 0.0071 |
| rel stdv |  |  |  | −9% | −12% | −12% |

| ave K-G12 | | | ave u-G12 | | |
|---|---|---|---|---|---|
| hours | loss, g | calc | hours | loss, g | calc |
| 1 | −0.0095 | −0.0096 | 1 | −0.0075 | −0.0074 |
| 2 | −0.0476 | −0.0473 | 2 | −0.0420 | −0.0423 |
| 2.5 | −0.0659 | −0.0661 | 2.5 | −0.0599 | −0.0597 |
| Multiple R | 0.99996 |  | Multiple R | 0.99995 |  |
| Intercept | 0.0280 |  | Intercept | 0.0275 |  |
| Rate, g/H | −0.0377 |  | Rate g/H | −0.0349 |  |

The average weight gain due to coating three rods of paper from Plant G, labeled K-G12-1 to 3, is about 0.040 g, as shown under the column labeled "1 coat" in the table above. The release rate was essentially unchanged by the coating: −0.0377 compared to −0.0349, and virtually the same, −0.0387 g/H, as seen previously. Because the 40 mg coat did not change the delivery rate, all the previously-coated rods were re-coated.

The second coat resulted in a weight gain of 56 and 57 mg for rods K-G12-1 and 3, and 73 mg for K-G12-2. The uneven nature of the weight gain was due to experimental variables. The average release rate is shown below in Table 21.

TABLE 21

| ave K-G12, 2 d coat, 9.5 H | calc | ave u-G12, 9.5 H | calc |
|---|---|---|---|
| 0.5 | −0.0136 | −0.0126 | 0.5 | −0.0198 | −0.0200 |
| 1 | −0.0249 | −0.0225 | 1 | −0.0392 | −0.0394 |
| 1.5 | −0.0338 | −0.0325 | 1.5 | −0.0590 | −0.0589 |
| 2.5 | −0.0508 | −0.0525 | 2.5 | −0.0980 | −0.0977 |
| 3.5 | −0.0715 | −0.0725 | 3.5 | −0.1365 | −0.1366 |
| 4.5 | −0.0879 | −0.0925 | 4.5 | −0.1759 | −0.1755 |
| 8.5 | −0.1734 | −0.1724 | 8.5 | −0.3306 | −0.3309 |
| 9.5 | −0.1940 | −0.1924 | 9.5 | −0.3698 | −0.3698 |
| Multiple R | 0.9994 |  | Multiple R | 1.0000 |  |
| Intercept | −0.0026 |  | Intercept | −0.0006 |  |
| Rate, g/H | −0.0200 |  | Rate, g/H | −0.0389 |  |

The average rate for coated rods was about 50% lower (−0.0200 vs. −0.0389 g/H) than that for un-coated rods. In addition, both sets of rods deliver their load linearly as shown by the best-fit straight-line results (Intercept+Rate×time in hours) shown under the column labeled "calc". Thus, the second coating produced the desired rate reduction.

Figure 7A:
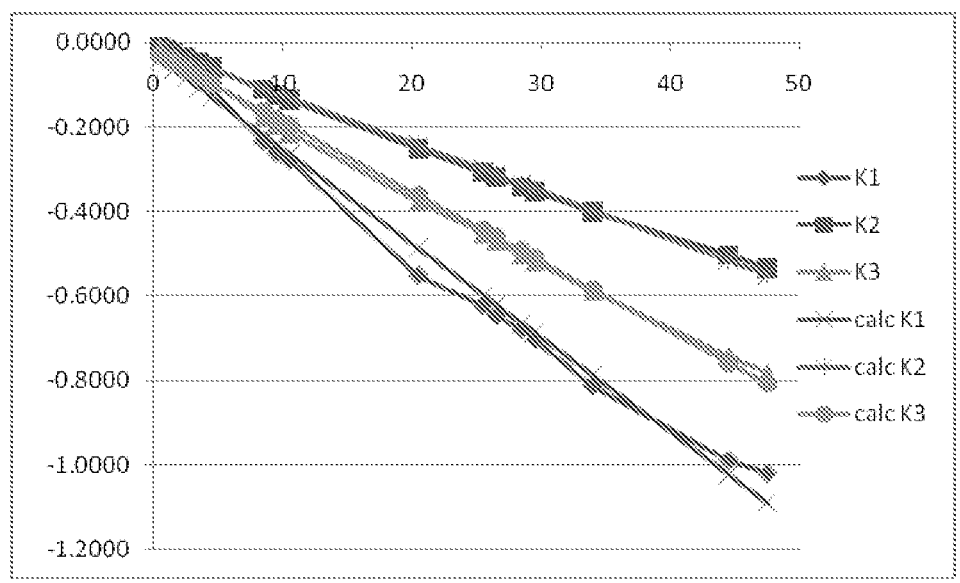
FIG. 7A is a graph of release from coated structural components.

The uneven nature of the coating produced uneven delivery rates as shown by FIG. 7A showing individual weight loss from coated rods. Y is grams wt vs time in hours (X axis)

Note that for coated rod K-G12-1, abbreviated K1 in the graph (diamond), the release, while linear, is somewhat erratic when compared to rods 2 (square) and 3 (triangles). The best-fit straight lines (calc K1-K3) are also shown for reference. Note also that the rod with the heaviest coating, K-G12-2 abbreviated K2—squares—in the graph, has the lowest release, 11.3 mg/H vs. 22.3 and 16.5 mg/H for K1 and K3. This is shown in Table 22.

TABLE 22

|  | abbreviation | | |
|---|---|---|---|
|  | K1 K-G12-1 | K2 K-G12-2 | K3 K-G12-3 |
| Multiple R | 0.9959 | 0.9991 | 0.9986 |
| Intercept | −0.0296 | −0.0120 | −0.0232 |
| Rate g/H | −0.0223 | −0.0113 | −0.0165 |

Figure 7B:
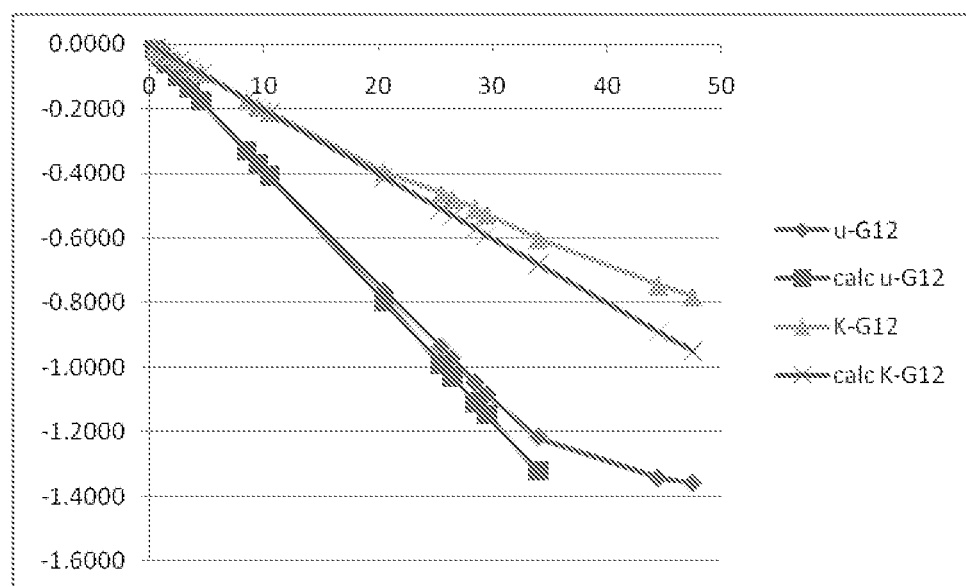
FIG. 7B is a graph of release from coated and uncoated structural components, where the y axis is wt loss in grams and the x axis is time in hours.

A consequence of the variance with time was that the average rate over an extended period of time (48 hours) is slightly different from that reported above for the period lasting 9.5 hours (−0.0200 vs. −0.0167 g/H). Another possible explanation is that the coating, after 48 hours, has hardened some more thereby reducing the rate compared to the early (less hard) coat. The FIG. 7B shows the average loss over time compared to the straight line fit obtained at 9.5 hours.

The load is 1.64 g per 5.5" rods of paper from Plant G. As seen below for the uncoated rods (diamonds) about 1.2 g are delivered linearly, or about 70% of the load, as previously reported for rods of paper from Plant G. The coated rods showed deviations from linearity maybe due to the lack of uniformity, or the changing nature of the Krylon coating as it cures over time. Nevertheless, it is clear that the coated rods were far from exhausted when compared to the uncoated rods (50% of load delivered at 48 hours compared to 70% of the load at 30-35 hours).

The same approach was used to follow the coating of 9.5" rods of paper from Plant D loaded with Douglas Fir. Covering paper rods with a glossy coating, delivered by the use of Krylon clear glaze, was a viable approach to modulate delivery rates.

What is claimed is:

1. A scented article comprising,
an absorbent matrix material wound about a central axis to form a multilayered rod;
at least one olfactory-active composition releasably retained in the absorbent matrix material;
at least a portion of an exterior surface of the rod treated with a porosity-altering material;
wherein the treated exterior surface of the rod has a first porosity, and at least one interior layer of the rod has a second porosity, wherein the second porosity is different from the first porosity;
wherein the porosity-altering material comprises a dye, pigment, a wax, soy wax, paraffin, bees wax, polyethylene wax, microcrystalline wax, waxes that soften or melt at a temperature greater than about 150 F, acrylates, polylactide, polyglycolide or polycaprolactone, or a polyester copolymer selected from poly(lactide/glycolide) acid (PLGA) or poly(lactid-co-epsilon-caprolact-one) (PLCL), alkyl- or alkoxyalkyl-2-cyanoacrylates, n-butyl-2-cyanoacrylate, 2-methoxybutyl-2-cyanoacrylate, crosslinked cyanoacrylate, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, copolymers of alkyl methacrylates and butadiene; dioctyl phthalate, dimethyl sebacate, trethyl phosphate, tri(2-ethylhexy) phosphate, tri(p-cresyl)phosphate, glyceryl triacetate, glyceryl tributyrate, diethyl sebacate, dioctyl adipate, isopropyl myristate, butyl stearate, lauric acid, dibutyl phthalate, trioctyl trimellitate, dioctyl glutarate, or a starch.

2. The scented article of claim 1, wherein the multilayered rod comprises a hollow core.

3. The scented article of claim 2, wherein an exposed surface of the hollow core is treated with a porosity-altering material such that a porosity of the treated exposed surface of the hollow core is different from the second porosity of the at least one interior layer.

4. The scented article of claim 1, wherein the porosity-altering material is configured to at least partially inhibit release of the at least one olfactory-active composition from the absorbent matrix material.

5. The scented article of claim 1, further comprising an engaging means for engaging the scented article with a surface, another article, or another structure.

6. The scented article of claim 5, wherein the engaging means comprises a clip, a hook, a circle, a hook and eye means, a string, prongs, a loop, adhesives, a spike, a holder, a vase, a container, and a receptacle.

7. The scented article of claim 1, wherein the multilayered rod is a spiral wound multilayered rod.

8. A scented article comprising:
an absorbent matrix material wound about a central axis to form a multilayered rod having a hollow core;
at least one olfactory-active composition releasably retained in the absorbent matrix material;
wherein at least a portion of exposed surfaces of the rod are treated with a porosity-altering material;
wherein a porosity of the treated exposed surfaces of the rod is different from a porosity of at least one non-exposed layer of the rod;
wherein the porosity-altering material comprises a dye, pigment, a wax, soy wax, paraffin, bees wax, polyethylene wax, microcrystalline wax, waxes that soften or melt at a temperature greater than about 150 F, acrylates, polylactide, polyglycolide or polycaprolactone, or a polyester copolymer selected from poly(lactide/glycolide) acid (PLGA) or poly(lactid-co-epsilon-caprolact-one) (PLCL), alkyl- or alkoxyalkyl-2-cyanoacrylates, n-butyl-2-cyanoacrylate, 2-methoxybutyl-2-cyanoacrylate, crosslinked cyanoacrylate, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, copolymers of alkyl methacrylates and butadiene; dioctyl phthalate, dimethyl sebacate, trethyl phosphate, tri(2-ethylhexy) phosphate, tri(p-cresyl)phosphate, glyceryl triacetate, glyceryl tributyrate, diethyl sebacate, dioctyl adipate, isopropyl myristate, butyl stearate, lauric acid, dibutyl phthalate, trioctyl trimellitate, dioctyl glutarate, or a starch.

9. The scented article of claim 8, wherein the porosity-altering material is configured to at least partially inhibit release of the at least one olfactory-active composition from the absorbent matrix material.

10. The scented article of claim 8, wherein the multilayered rod is a spiral wound multilayered rod.

11. A scented article comprising
an absorbent matrix material wound about a central axis to form a multilayered rod;
at least one olfactory-active composition releasably retained in the absorbent matrix material;
a barrier material applied to at least a portion of an exterior surface of the rod;
wherein the barrier material retards a release of the at least one olfactory-active composition through the exterior surface of the rod; and
wherein the barrier material comprises a paper wrapping, dye, pigment, a wax, soy wax, paraffin, bees wax, polyethylene wax, microcrystalline wax, waxes that soften or melt at a temperature greater than about 150 F, acrylates, polylactide, polyglycolide or polycaprolactone, or a polyester copolymer selected from poly (lactide/glycolide) acid (PLGA) or poly(lactid-co-epsilon-caprolact-one) (PLCL), alkyl- or alkoxyalkyl-2-cyanoacrylates, n-butyl-2-cyanoacrylate, 2-methoxybutyl-2-cyanoacrylate, crosslinked cyanoacrylate, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, copolymers of alkyl methacrylates and butadiene; dioctyl phthalate, dimethyl sebacate, trethyl phosphate, tri(2-ethylhexy)phosphate, tri(p-cresyl)phosphate, glyceryl triacetate, glyceryl tributyrate, diethyl sebacate, dioctyl adipate, isopropyl myristate, butyl stearate, lauric acid, dibutyl phthalate, trioctyl trimellitate, dioctyl glutarate, or a starch.

12. The scented article of claim 11, wherein the multilayered rod comprises a hollow core.

13. The scented article of claim 11, further comprising an engaging means for engaging the scented article with a surface, another article, or another structure.

14. The scented article of claim 13, wherein the engaging means comprises a clip, a hook, a circle, a hook and eye means, a string, prongs, a loop, adhesives, a spike, a holder, a vase, a container, and a receptacle.

15. The scented article of claim 11, wherein the multilayered rod is a spiral wound multilayered rod.

16. A scented article comprising
an absorbent matrix material wound around a central axis using a spiral winding process to form a multilayered rod having a hollow core;
at least one olfactory-active composition releasably retained in the absorbent matrix material;
wherein the rod comprises at least one innermost ply, at least one outermost ply, and at least one middle ply, wherein each ply is formed by a complete revolution of the absorbent matrix material around the central axis;
wherein the at least one innermost ply and/or the at least one outermost ply has a different rate of absorbency than the at least one middle ply.

17. The scented article of claim 16, wherein at least some exposed surfaces of the rod are treated with a porosity-altering material.

18. The scented article of claim 17, wherein the porosity-altering material is configured to at least partially inhibit release of the at least one olfactory-active composition from the absorbent matrix material.

19. The scented article of claim 16, further comprising an engaging means for engaging the scented article with a surface, another article, or another structure.

20. The scented article of claim 19, wherein the engaging means comprises a clip, a hook, a circle, a hook and eye means, a string, prongs, a loop, adhesives, a spike, a holder, a vase, a container, and a receptacle.

* * * * *